US012582476B2

(12) United States Patent
Wagner et al.

(10) Patent No.: US 12,582,476 B2
(45) Date of Patent: Mar. 24, 2026

(54) SYSTEMS FOR PLANNING AND PERFORMING BIOPSY PROCEDURES AND ASSOCIATED METHODS

(71) Applicant: Intuitive Surgical Operations, Inc., Sunnyvale, CA (US)

(72) Inventors: Oliver J. Wagner, Mountain View, CA (US); Tao Zhao, Sunnyvale, CA (US); Federico Barbagli, San Francisco, CA (US); Christopher R. Carlson, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 429 days.

(21) Appl. No.: 18/041,337

(22) PCT Filed: Aug. 6, 2021

(86) PCT No.: PCT/US2021/045076
§ 371 (c)(1),
(2) Date: Feb. 10, 2023

(87) PCT Pub. No.: WO2022/035709
PCT Pub. Date: Feb. 17, 2022

(65) Prior Publication Data
US 2023/0285081 A1 Sep. 14, 2023

Related U.S. Application Data

(60) Provisional application No. 63/064,111, filed on Aug. 11, 2020.

(51) Int. Cl.
*A61B 34/10* (2016.01)
*G06T 7/11* (2017.01)

(52) U.S. Cl.
CPC ................ *A61B 34/10* (2016.02); *G06T 7/11* (2017.01); *A61B 2034/105* (2016.02); *G06T 2207/30004* (2013.01)

(58) Field of Classification Search
CPC ............. G06T 7/11; G06T 2207/20081; A61B 2017/00809; A61B 34/00; A61B 34/10;
(Continued)

(56) References Cited

U.S. PATENT DOCUMENTS

| | | |
|---|---|---|
| 6,389,187 B1 | 5/2002 | Greenaway et al. |
| 7,772,541 B2 | 8/2010 | Froggatt et al. |

(Continued)

OTHER PUBLICATIONS

International Preliminary Report on Patentability for Application No. PCT/US2021/045076 mailed Feb. 23, 2023, 9 pages.
(Continued)

*Primary Examiner* — Katrina R Fujita
(74) *Attorney, Agent, or Firm* — Haynes & Boone, LLP.

(57) ABSTRACT

Disclosed herein are devices, systems, methods, and computer program products for planning and performing medical procedures. In some embodiments, a system for planning a medical procedure includes a processor and a memory operably coupled to the processor. The memory can store instructions that, when executed by the processor, cause the system to perform operations including: receiving image data of an anatomic region including a plurality of lymph nodes and a target lesion; generating a three-dimensional model of the anatomic region by segmenting the image data; selecting a subset of the lymph nodes to be biopsied during the medical procedure based at least in part on a location of the target lesion in the three-dimensional model; and determining a sequence for navigating a biopsy device to locations of the subset of the lymph nodes during the medical procedure.

20 Claims, 8 Drawing Sheets

(58) Field of Classification Search
CPC ......... A61B 34/20; A61B 34/25; A61B 34/37;
A61B 2034/105; A61B 2034/107; A61B
2034/301
See application file for complete search history.

(56) References Cited

U.S. PATENT DOCUMENTS

| | | | |
|---|---|---|---|
| 7,781,724 B2 | 8/2010 | Childers et al. | |
| 10,373,719 B2 | 8/2019 | Soper et al. | |
| 10,706,543 B2 | 7/2020 | Donhowe et al. | |
| 11,202,680 B2 | 12/2021 | Donhowe et al. | |
| 2006/0013523 A1 | 1/2006 | Childlers et al. | |
| 2010/0310146 A1 | 12/2010 | Higgins et al. | |
| 2018/0333095 A1 | 11/2018 | Sartor et al. | |
| 2019/0231287 A1* | 8/2019 | Krimsky | A61B 8/466 |
| 2019/0247127 A1 | 8/2019 | Kopel et al. | |
| 2020/0030044 A1 | 1/2020 | Wang et al. | |
| 2020/0193594 A1* | 6/2020 | Georgescu | G06T 7/11 |

OTHER PUBLICATIONS

International Search Report and Written Opinion for Application No. PCT/US2021/045076, mailed on Nov. 11, 2021, 14 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

_210_
Receive image data of an anatomic region
of a patient

_220_
Generate a 3D model of the anatomic region by
segmenting the image data

_230_
Select lymph node sites to be biopsied

_240_
Determine a sequence for biopsying the selected
lymph node sites

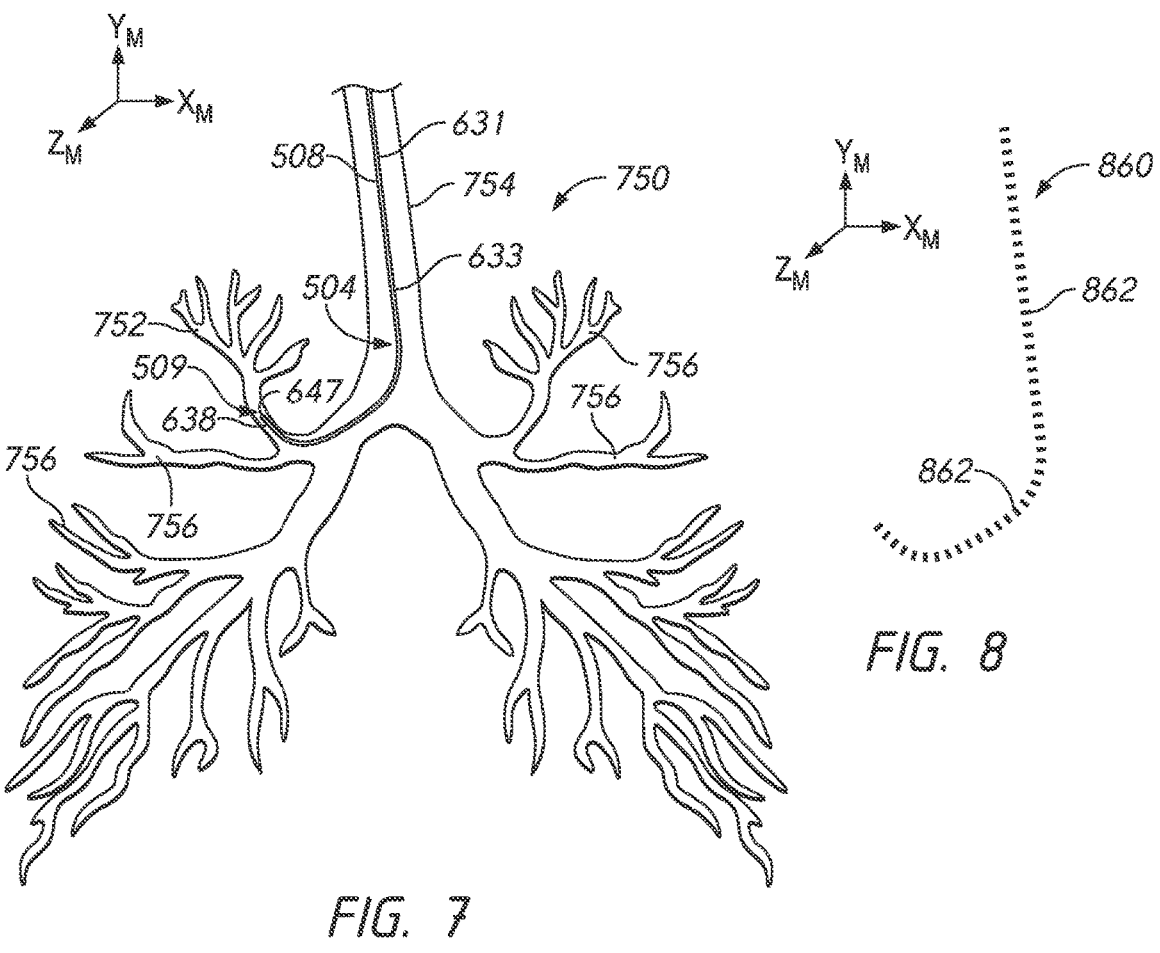
*FIG. 7*
*FIG. 8*
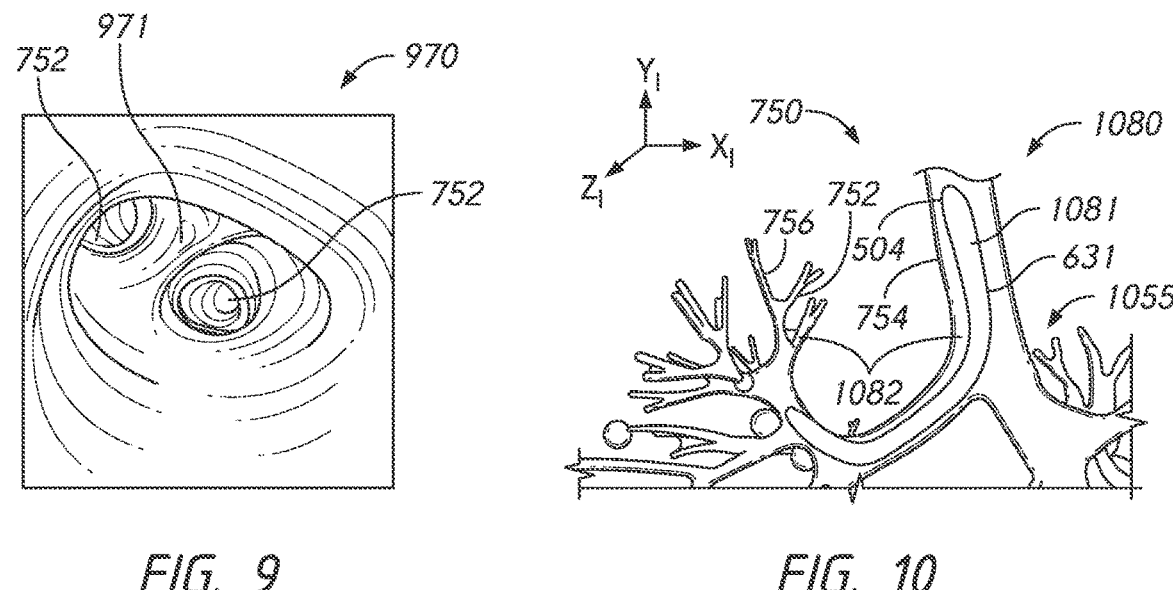
*FIG. 9*
*FIG. 10*

SYSTEMS FOR PLANNING AND PERFORMING BIOPSY PROCEDURES AND ASSOCIATED METHODS

CROSS-REFERENCE TO RELATED APPLICATION(S)

This patent application is the U.S. National Stage patent application of International Patent Application No. PCT/US2021/045076 filed Aug. 6, 2021 which claims priority to and the benefit of U.S. Provisional Application No. 63/064,111, filed Aug. 11, 2020, each of which is incorporated herein by reference in its entirety.

TECHNICAL FIELD

The present disclosure is directed to systems, methods, and computer program products for planning and performing biopsy procedures.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways. Improved systems and methods are needed to accurately perform registrations between medical tools and images of the anatomic passageways.

SUMMARY

Disclosed herein are devices, systems, methods, and computer program products for planning medical procedures, including selecting lymph nodes and/or lymph node stations to be biopsied and determining a sequence for biopsying the selected lymph nodes and/or lymph node stations. In some embodiments, a system for planning a medical procedure includes a processor and a memory operably coupled to the processor. The memory can store instructions that, when executed by the processor, cause the system to perform operations including receiving image data of an anatomic region of a patient. The anatomic region can include a plurality of lymph nodes and a target lesion. The operations can also include generating a three-dimensional model of the anatomic region by segmenting the image data. The three-dimensional model can include a plurality of segmented components corresponding to the plurality of lymph nodes and the target lesion. The operations can further include selecting a subset of the lymph nodes to be biopsied during the medical procedure based at least in part on a location of the target lesion in the three-dimensional model, and determining a sequence for navigating a biopsy device to locations of the subset of the lymph nodes during the medical procedure.

In these and other embodiments, a non-transitory, computer-readable medium can store instructions thereon that, when executed by one or more processors of a computing system, cause the computing system to perform operations including receiving image data of an anatomic region of a patient, the anatomic region having a plurality of lymph nodes and a target lesion. The operations can also include generating a three-dimensional model of the anatomic region by segmenting the image data, the three-dimensional model having a plurality of segmented components corresponding to the plurality of lymph nodes and the target lesion. The operations can further include selecting a subset of the lymph nodes to be biopsied during a medical procedure based at least in part on a location of the target lesion in the three-dimensional model, and determining a sequence for navigating a biopsy device to locations of the subset of the lymph nodes during the medical procedure.

In these and still other embodiments, a method can include receiving image data of an anatomic region of a patient, the anatomic region having a plurality of lymph nodes and a target lesion; generating a three-dimensional model of the anatomic region by segmenting the image data, the three-dimensional model having a plurality of segmented components corresponding to the plurality of lymph nodes and the target lesion; selecting a subset of the lymph nodes to be biopsied during a medical procedure based at least in part on a location of the target lesion in the three-dimensional model; and determining a sequence for navigating a biopsy device to locations of the subset of the lymph nodes during the medical procedure.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

FIGS. 1A-1C illustrate lymph node stations of a thoracic region of a patient.

FIG. 7 is a schematic representation of a portion of the medical instrument system of FIG. 6 extended within an anatomic region of a patient in accordance with various embodiments of the present technology.

FIG. 8 illustrates a plurality of coordinate points forming a point cloud representing a shape of the portion of the medical instrument system of FIG. 7 configured in accordance with various embodiments of the present technology.

FIG. 9 illustrates a real navigational image of real patient anatomy from a viewpoint of the portion of the medical instrument system of FIG. 7 extended within the anatomic region of FIG. 8 in accordance with various embodiments of the present technology.

FIG. 10 illustrates an intraoperative image of a portion of the anatomic region of FIG. 8 while the portion of the medical instrument system of FIG. 7 is extended within the anatomic region in accordance with various embodiments of the present technology.

Figure 6:
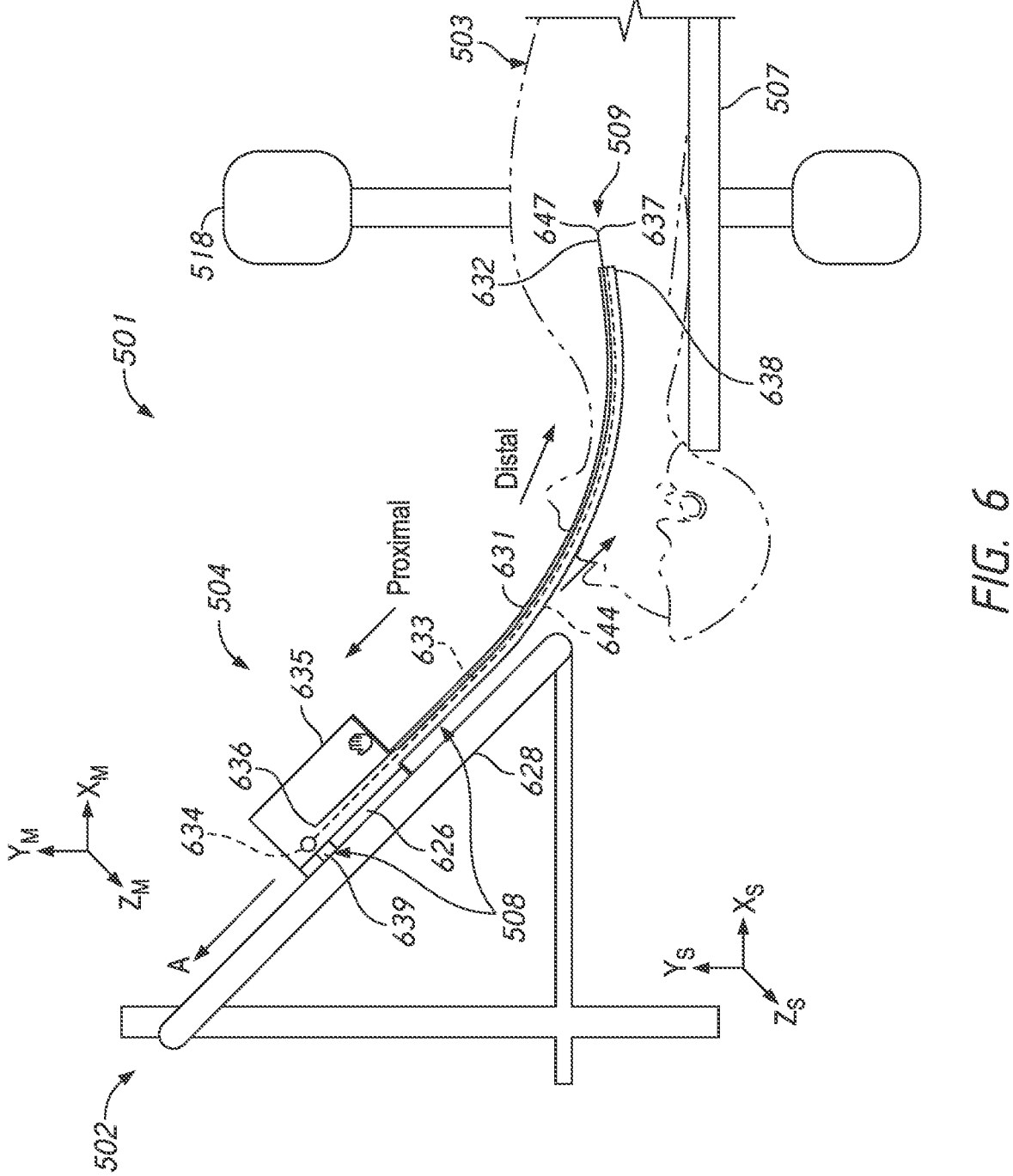
FIG. 6 is a schematic representation of a manipulator assembly, a medical instrument system, and an imaging system configured in accordance with various embodiments of the present technology.
Figure 11:
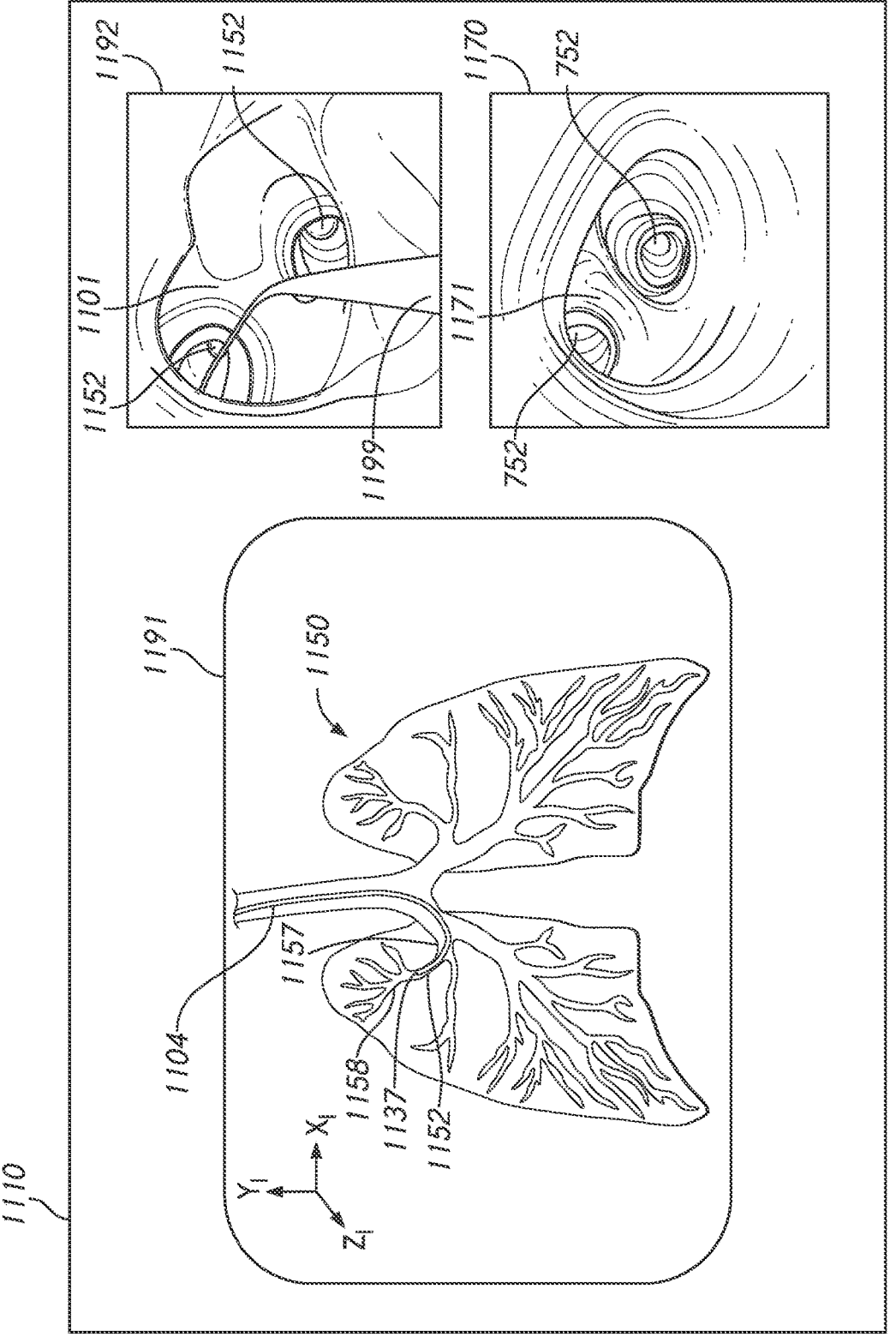

FIG. 11 is a schematic representation of a display of a display system displaying a composite virtual navigational image in which the medical instrument system of FIGS. 6 and 7 is registered to an anatomic model of the anatomic region of FIG. 7, a virtual navigational image of virtual patient anatomy, and a real navigational image of real patient anatomy within the anatomic region in accordance with various embodiments of the present technology.

DETAILED DESCRIPTION

The present disclosure is directed to devices, systems, methods, and computer program products for planning and/or performing a biopsy procedure within an anatomic region of a patient. In some embodiments, for example, the biopsy procedure is performed on a cancer patient to determine the anatomic extent of the cancer ("cancer staging"). The cancer staging process can include determining how much cancer is in the patient's body, where the cancer is located, and/or whether the cancer has spread from its original site (e.g., to the lymphatic drainage system, vasculature, other organ systems, etc.). For example, in the context of lung cancer (e.g., non-small cell lung cancer), a staging process can include biopsying multiple lymph nodes and/or lymph node stations (i.e., clinically-defined groupings of lymph nodes) near the airways of the lungs. Accurate staging is important for assessing patient prognosis and selecting the appropriate course of treatment. In some instances, for example, surgery may be recommended for early stage lung cancers, but may be contraindicated for later stage lung cancers. However, an operator performing a biopsy procedure may not be aware of clinically-recommended staging guidelines (e.g., which lymph nodes and/or lymph node stations should be biopsied), may not know how to apply the guidelines to the particular patient's pathology, and/or may not know how to perform the biopsy procedure efficiently while complying with the guidelines.

Accordingly, the present technology can aid an operator in planning and/or performing a biopsy procedure by (i) identifying which lymph nodes and/or lymph node stations (collectively, "lymph node sites") should be biopsied, and (ii) determining a sequence for biopsying the selected lymph node sites. In some embodiments, for example, a three-dimensional (3D) model of an anatomic region of a patient is generated (e.g., from preoperative image data) and segmented into components representing anatomic structures such as the airways, lungs, lymph nodes, vessels, and/or a target lesion. The segmented model can be used to select lymph node sites to be biopsied (e.g., based on the location of the target lesion, locations of the lymph node sites, lymphatic drainage pathways, clinical staging guidelines, etc.). The model can also be used to determine a sequence for biopsying the selected lymph node sites in an efficient manner while minimizing risk of cross-contamination. During the biopsy procedure, the selected lymph node sites and the biopsy sequence can be displayed to provide visual guidance to the operator and to facilitate navigation within the patient anatomy. The present technology is expected to increase operator compliance with clinical staging guidelines, as well as improve the efficiency and accuracy of the staging process, which may contribute to better patient outcomes.

A. Embodiments of Techniques for Planning and Performing Biopsy Procedures

The present technology is generally directed to planning and/or performing a medical procedure, such as a biopsy procedure for diagnosing a disease or condition of a patient. In some embodiments, for example, the systems described herein are configured to plan a biopsy procedure for staging a lung cancer (e.g., non-small cell lung cancer). The stages of lung cancer can be defined as follows:

Stage 0: The cancer has not spread from its original site ("in situ disease").

Stage I: A small primary tumor located in only one lung that has not spread to any lymph nodes and has not metastasized.

Stage II: Either a larger primary tumor that has not spread to any lymph nodes or a smaller tumor in the lung that has spread to nearby lymph nodes.

Stage III: Cancer is found in the lung and in the lymph nodes in the middle of the chest ("locally advanced disease"). Stage III has two subtypes: IIIA (the cancer has spread only to lymph nodes on the same side of the chest where the cancer started) and IIIB (the cancer has spread to the lymph nodes on the opposite side of the chest and/or above the collar bone).

Stage IV: The cancer has spread to both lungs, to fluid in the area around the lungs, or to another part of the body, such as the liver or other organs ("advanced disease").

As discussed above, accurate lung cancer staging may be important for assessing patient prognosis and/or determining the appropriate treatment options. For example, surgery may be recommended for patients with Stage 0 or Stage I cancer; treatment (e.g., chemotherapy, radiation therapy, radiochemotherapy, immunotherapy) followed by surgery may be recommended for patients with Stage II cancer; and treatment (e.g., chemotherapy, radiation therapy, radiochemotherapy, immunotherapy) without surgery may be recommended for patients with Stage III or Stage IV cancer.

In some embodiments, lung cancer staging involves obtaining tissue samples from one or more lymph node sites within a thoracic region of the patient. As described above, the presence of cancer cells at certain lymph node sites (e.g., lymph node stations in the middle of the chest, lymph node stations on the opposite side of the chest from the original cancer site, etc.) may correlate to more advanced stages of cancer. Accordingly, the extent and severity of the cancer can be assessed by systematically sampling lymph nodes from different lymph node stations in the thoracic region.

Figure 1A:
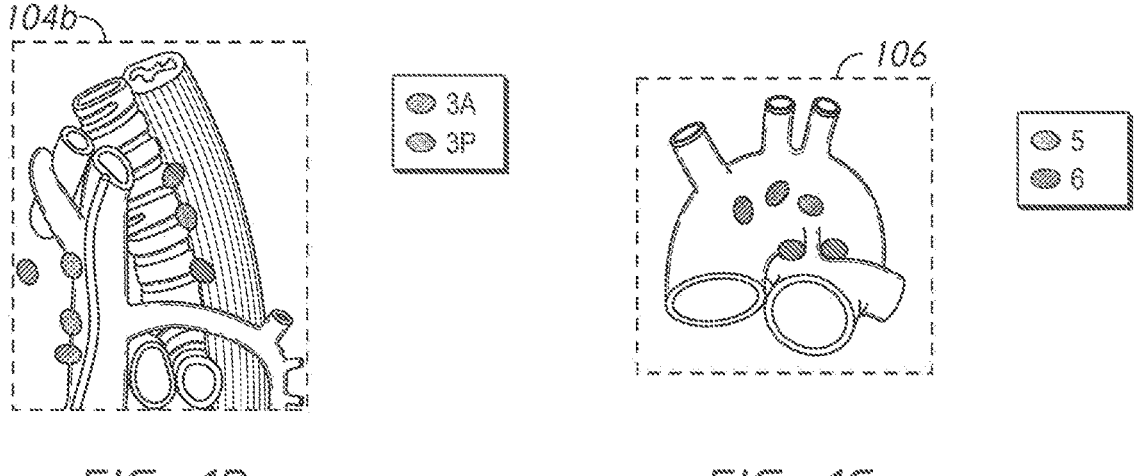

FIGS. 1A-1C illustrate lymph node stations of a thoracic region 100 of a patient. As can be seen in FIGS. 1A-1C and in Table 1 below, the lymph nodes of the thoracic region 100 can be grouped into 14 different lymph node stations (stations 1R-14). The lymph node stations can be grouped into 7 anatomic zones (102-114, indicated by broken lines in FIGS. 1A-1C).

TABLE 1

Thoracic Lymph Node Stations

Supraclavicular zone (102)
Station 1R: Right low cervical, supraclavicular, and sternal notch lymph nodes
Station 1L: Left low cervical, supraclavicular, and sternal notch lymph nodes
Upper zone (superior mediastinal lymph nodes) (104a, 104b)
Station 2R: Right upper paratracheal lymph nodes
Station 2L: Left upper paratracheal lymph nodes
Station 3A: Prevascular lymph nodes
Station 3P: Retrotracheal lymph nodes
Station 4R: Right lower paratracheal lymph nodes
Station 4L: Left lower paratracheal lymph nodes
Aortopulmonary zone (106)
Station 5: Subaortic lymph nodes
Station 6: Paraaortic lymph nodes
Subcarinal zone (108)
Station 7: Subcarinal lymph nodes
Lower zone (inferior mediastinal lymph nodes) (110)
Stations 8R, 8L: Paraesophageal lymph nodes
Stations 9R, 9L: Pulmonary ligament lymph nodes
Hilar and interlobar zone (pulmonary lymph nodes) (112)
Stations 10R, 10L: Hilar lymph nodes
Stations 11R, 11L: Interlobar lymph nodes
Peripheral zone (pulmonary lymph nodes) (114)
Stations 12R, 12L: Lobar lymph nodes
Stations 13R, 13L: Segmental lymph nodes
Stations 14R, 14L: Subsegmental lymph nodes As described in greater detail below, the systems described herein can be configured to select one or more of the lymph node sites shown in FIGS. 1A-IC and Table 1 to be biopsied during a medical procedure for staging lung cancer.

Figure 2:
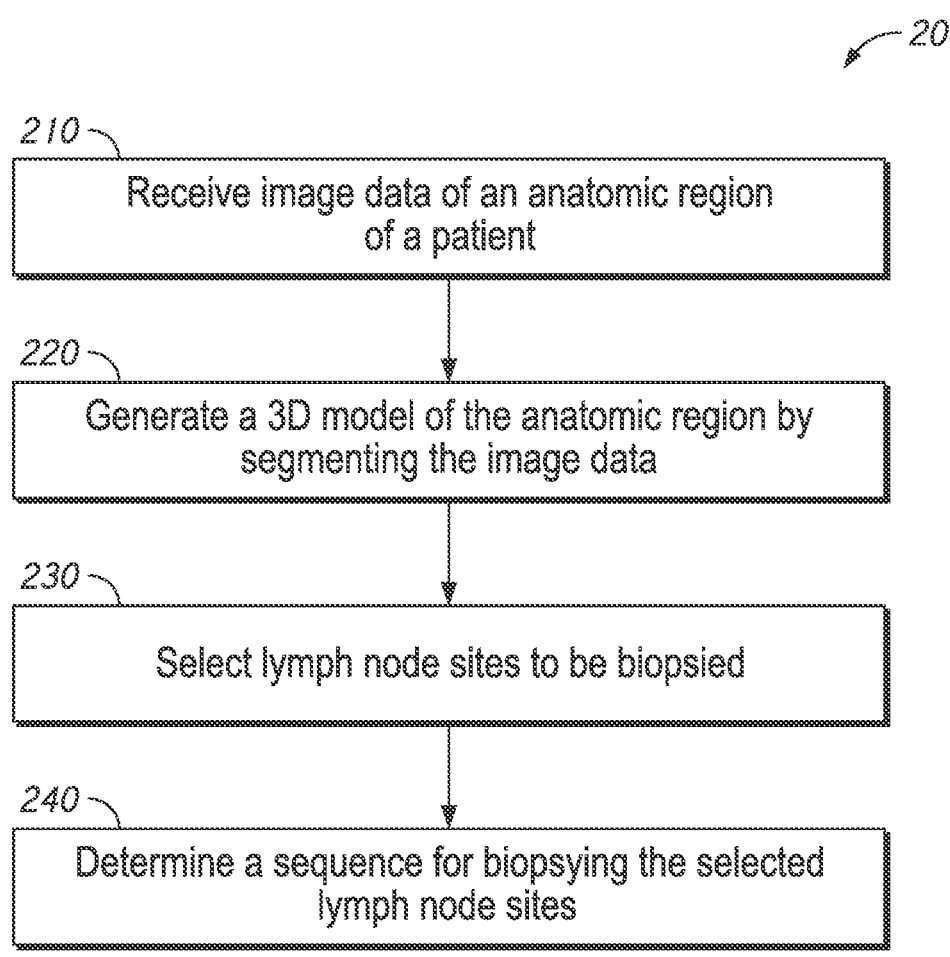
FIG. 2 is a flow diagram illustrating a method for planning a biopsy procedure in accordance with various embodiments of the present technology.

FIG. 2 is a flow diagram illustrating a method 200 for planning a biopsy procedure in accordance with various embodiments of the present technology. The method 200 is illustrated as a set of steps or processes 210-240. All or a subset of the steps of the method 200 can be implemented by a computing system or device, such as a workstation configured to perform preoperative planning for a medical procedure. Alternatively or in combination, all or a subset of the steps of the method 200 can be implemented by a control system of a medical instrument system or device, including various components or devices of a robotic or teleoperated system, as described in greater detail below. The computing system for implementing the method 200 can include one or more processors operably coupled to a memory storing instructions that, when executed, cause the computing system to perform operations in accordance with the steps 210-240.

The method 200 begins at step 210 with receiving image data of an anatomic region of a patient. The image data can include, for example, computed tomography (CT) data, magnetic resonance imaging (MRI) data, fluoroscopy data, thermography data, ultrasound data, optical coherence tomography (OCT) data, thermal image data, impedance data, laser image data, nanotube X-ray image data, and/or other suitable data representing the anatomic region where the biopsy procedure is to be performed. The image data can correspond to two-dimensional (2D), 3D, or four-dimensional (e.g., time-based or velocity-based information) images. In some embodiments, for example, the image data includes 2D images from multiple perspectives that can be combined into pseudo-3D images. The image data can be preoperative image data that is obtained before the biopsy procedure is performed on the patient.

At step 220, a 3D model of the anatomic region is generated by segmenting the image data. The model can represent the anatomic region in which the biopsy procedure is to be performed (e.g., the airways of the patient's lungs), and can represent the locations, shapes, and connectivity of the passageways and other structures (e.g., lymph nodes, target lesion, vessels, etc.) within that region. In some embodiments, the model includes a plurality of segmented components corresponding to anatomic structures or features within the anatomic region. Examples of anatomic structures or features that may be included in the model include one or more of the following: airways (e.g., trachea, main carina, left main bronchus, right main bronchus, and/or sub-segmental bronchus), lymph nodes (e.g., any of the lymph node sites described with respect to FIGS. 1A-1C and Table 1), vessels (e.g., aorta, superior vena cava, pulmonary trunk), lungs, and/or a target lesion (e.g., a tumor or other tissue site that is known or suspected to be cancerous).

The 3D model can be generated by segmenting graphical elements in the image data that represent or otherwise correspond to the anatomic structures or features. During the segmentation process, pixels or voxels generated from the image data may be partitioned into segments or elements and/or be tagged to indicate that they share certain characteristics or computed properties such as color, density, intensity, and texture. The segments or elements associated with anatomical features of the patient are then converted into a segmented anatomic model, which is generated in a model or image reference frame. To represent the model, the segmentation process may delineate sets of voxels representing the anatomic region and then apply a function, such as marching cube function, to generate a 3D surface that encloses the voxels. The model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically. Various systems and methods for segmenting anatomic structures from image data are described in further detail in U.S. Patent Application Publication No. 2020/0030044 (filed Apr. 18, 2018) (disclosing a graphical user interface for planning a procedure); and U.S. U.S. Pat. No. 10,373, 719 (filed Sep. 3, 2015) (disclosing systems and methods for pre-operative modeling); both of which are incorporated by reference herein in their entireties.

In some embodiments, step 220 includes segmenting a plurality of lymph nodes in the image data. Segmenting of the lymph nodes can include, for example, analyzing the image data to identify graphical elements that correspond to lymph nodes, rather than other anatomic structures such as airways, vessels, etc. In some embodiments, lymph nodes are identified based on characteristics such as shape (e.g., oval or round, not tubular), size (e.g., approximately 1 cm in diameter), and/or location (e.g., near airways and/or within anatomic zones corresponding to lymph node stations). Once identified, the lymph nodes can be segmented into individual model components as discussed above. Optionally, step 220 can further include assigning each segmented lymph node to a lymph node station (e.g., based on the location of the lymph node relative to other anatomic structures).

The lymph node segmentation procedure can be performed in various ways, such as automatically (e.g., without requiring any operator input to identify the lymph nodes), semi-automatically (e.g., with some operator input), or manually by the operator. For example, automatic lymph node segmentation can be performed using a machine learning algorithm, such as a deep learning algorithm (e.g., a convolutional neural network or other type of neural network) that has been trained to identify and segment individual lymph nodes from CT scans or other image data of the patient anatomy. Training of the machine learning algorithm can be performed, for example, via supervised learning techniques using large sets of image data in which the lymph nodes have already been identified. Once trained, the machine learning algorithm can automatically recognize graphical elements in the image data that are likely to correspond to lymph nodes, and can segment those graphical elements to create individual model components, as discussed above. Optionally, the machine learning algorithm can also be trained to automatically identify and segment other anatomic structures (e.g., airways, lesions, vessels, etc.).

A semi-automatic lymph node segmentation process can involve some steps that are performed automatically and some steps that are performed based on input from the operator. For example, the operator can select one or more locations in the image data that include lymph nodes and/or correspond to lymph node stations, and the computing system can analyze the selected locations to identify and segment the lymph nodes at those locations. In some embodiments, the operator provides input indicating the selected locations (e.g., via a suitable graphical user interface), such as by clicking or otherwise marking a point corresponding to a lymph node, drawing a boundary around edges or surfaces of a lymph node, selecting areas of the image data including lymph nodes and/or lymph node stations, or any other suitable process. The system can then use the input from the operator as a starting point for automatically detecting one or more lymph nodes in the image data. For example, the system may use edge detection algorithms, machine learning algorithms, etc. to search the image locations indicated by the operator for objects that are likely to correspond to lymph nodes. The results can be displayed to the operator for approval, rejection, modification, or other feedback. Alternatively or in combination, the system can automatically provide an initial selection of potential lymph nodes and the operator can accept, reject, or modify the selections. Optionally, if identification of individual lymph nodes is challenging (e.g., due to a low signal to noise ratio in the image data), the system and/or operator can instead identify and segment locations in the image data that correspond to lymph node stations (e.g., the lymph node stations and/or anatomic zones described above with respect to FIGS. 1A-1C), rather than identifying and segmenting individual lymph nodes.

Figure 3:
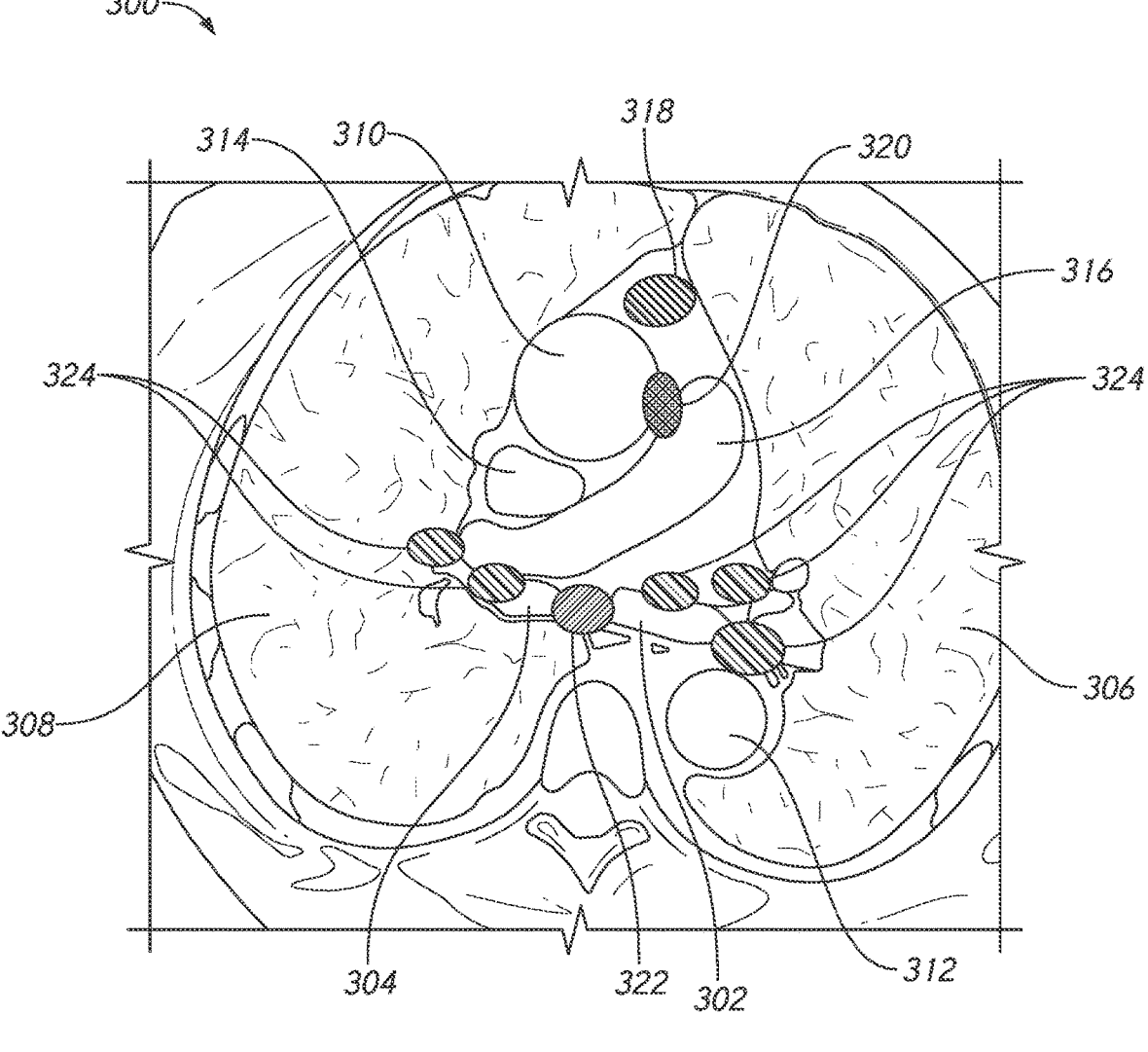
FIG. 3 is a computed tomography image of a patient's thoracic region.

FIG. 3, for example, is a CT image 300 of a patient's thoracic region. The image 300 includes graphical elements representing various anatomic structures such as airways (e.g., left main bronchus 302, right main bronchus 304), left lung 306, right lung 308, vessels (e.g., ascending aorta 310, descending aorta 312, superior vena cava 314, pulmonary trunk 316), and a plurality of lymph nodes (e.g., prevascular lymph node 318 (station 3A), subaortic lymph node 320 (station 5), subcarinal lymph node 322 (station 7), and hilar lymph nodes 324 (station 10)). The processes described above with respect to step 220 of FIG. 2 can be used to automatically, semi-automatically, or manually segment the image 300 to create a 3D model of the thoracic region. The model can include segmented model components representing the airways (e.g., left main bronchus 302, right main bronchus 304) and the lymph nodes 318-324. Optionally, the model can also include segmented model components corresponding to the lungs (e.g., left lung 306, right lung 308), vessels (e.g., ascending aorta 310, descending aorta 312, superior vena cava 314, pulmonary trunk 316), and/or other anatomic structures such as a target lesion (not shown).

Referring back to FIG. 2, at step 230, one or more lymph node sites are selected. As discussed above, the selected lymph node sites can be biopsied to determine the stage of the patient's cancer, e.g., by assessing whether the cancer has spread from an initial site (e.g., a target lesion) to the lymph node sites. For example, the cancer may be early stage cancer if lymph node sites located near to the target lesion test negative for malignant cells. Conversely, the cancer may be advanced cancer if lymph node sites located away from the target test positive for malignant cells. The number of positive lymph node sites may also correlate to the extent of the cancer, e.g., the cancer may be early stage if few or none of the biopsied lymph node sites test positive, and may be advanced stage if most or all of the biopsied lymph node sites test positive. Accordingly, step 230 can involve selecting which lymph node sites should be biopsied in order to accurately stage the patient's cancer. Step 230 can involve selecting one or more individual lymph nodes, one or more lymph node stations, or a combination thereof. In some embodiments, for example, one or more lymph node stations are selected without specifying any particular lymph nodes within that station to be biopsied. In other embodiments one or more specific lymph nodes can be selected, with or without specifying the corresponding lymph node stations.

The selection of the lymph node sites can be based on the particular patient's pathology, such as the location of the target lesion in the patient. For example, step 230 can include selecting one or more lymph node sites that are located downstream along the lymphatic drainage pathway of the target lesion (e.g., sentinel lymph nodes). The drainage pathways within the patient's anatomic region can be determined based on clinical guidelines or research, the patient's particular anatomy and physiology, and/or any other suitable considerations. For example, in the thoracic region, drainage pathways can generally proceed from lymph node stations at the peripheral portions of the lungs to the lymph node stations at the mediastinum between the lungs. Drainage pathways typically do not cross the lobe or to the other side of the peripheral lung. Accordingly, if the target lesion is located at the peripheral portion of the lung (e.g., near station 13R—FIG. 1A), step 230 can involve selecting some or all the lymph node sites that are located between the target lesion and the mediastinum (e.g., stations 12R, 11R, and 10R—FIG. 1A), as well as mediastinal lymph node sites (e.g., stations 4R and 7—FIG. 1A). Optionally, lymph node sites that are located upstream from the target lesion (e.g., station 14R—FIG. 1A) and/or are not located along the drainage pathways from the target lesion (e.g., stations 14L, 13L, 12L—FIG. 1A) can be omitted. One of skill in the art will appreciate that drainage pathways may vary to some extent from patient to patient, and may skip over lymph node stations and/or pass between lymph node stations. Accordingly, the selection process of step 230 can be customized to each patient's particular anatomy and/or other clinical considerations.

Alternatively or in combination, the lymph node sites can be selected based on their location, such as their proximity to the target lesion. Proximity can be assessed quantitively (e.g., based on the measured distance between the target lesion and the lymph node site) and/or qualitatively (e.g., whether the lymph node site is on the same side of the chest as the target lesion, in the middle of the chest, or on the opposite side of the chest as the target lesion). In some embodiments, step 230 involves selecting lymph node sites at different proximities to the target lesion. For example, the selection can include at least one lymph node site on the same side of the chest as the target lesion (ipsilateral or "N1 nodes"), at least one lymph node site in the middle of the chest ("N2 nodes"), and at least one lymph node site on the opposite side of the chest as the target lesion (contralateral or "N3 nodes"). For example, if the target lesion is near station 13R (FIG. 1A), step 230 can involve selecting ipsilateral lymph node sites (e.g., stations 12R. 11R, 10R, and 4R—FIG. 1A) and/or contralateral lymph node sites (e.g., 12L, 11L, 10L, and 4L—FIG. 1A). Optionally, step 230 can involve selecting more lymph node sites that are close to the target lesion (e.g., N1 nodes) and fewer lymph node sites that are far from the target lesion (e.g., N2 nodes, N3 nodes). Lymph node sites that are very far from the target lesion or otherwise unlikely to have metastasis can be excluded.

In some embodiments, the lymph node sites are selected based on predictive modeling. Predictive modeling, for example, can be used to predict which lymph node sites are likely to have metastasis, based on the location of the target lesion, and can be performed using statistical models, machine learning models, or any other suitable technique. The predictive model can generate a risk score for each lymph node site representing the probability that the cancer has metastasized to the particular site. Lymph node sites associated with a higher risk score can be selected for biopsy, while lymph node sites associated with a lower risk score can be excluded.

Alternatively or in combination, the lymph node sites can be selected based on other parameters, such as one or more of the following: accessibility to the biopsy device (e.g., lymph nodes located near airways that are too narrow, too tortuous, or otherwise inaccessible to the biopsy device can be excluded), lymph node size (e.g., lymph nodes that are larger than 1 cm in diameter and/or larger than 5 mm in short-axis diameter can be selected), lymph node shape (e.g., lymph nodes that are abnormally-shaped can be selected), proximity to vulnerable anatomic structures (e.g., lymph node sites that are too close to major blood vessels, lung pleura, large bullae, etc. can be excluded), spatial relationships between lymph node sites and other anatomic structures (e.g., airways, lungs, lung nodules), patient-specific physiology, clinical guidelines or research (e.g., relating to cancer staging procedures), and the like.

Any suitable number and combination of lymph node sites can be selected. In some embodiments, step 230 involves selecting at least one, two, three, four, five, or more different lymph node sites to be biopsied (e.g., at least one, two, three, four, five, or more different lymph node stations). Optionally, step 230 can involve selecting a certain number of lymph nodes per station to be biopsied (e.g., at least one, two, three, or more lymph nodes). In some embodiments, certain lymph node sites are always selected, such as the mediastinal lymph nodes (e.g., some or all of lymph node stations 2L, 2R, 3A, 3P, 4L, 4R, 8L, 8R, 9L, 9R—FIG. 1A).

The selection of the lymph node sites can be performed automatically, semi-automatically, or manually. For example, the system can automatically analyze the locations of the target lesion, the lymph nodes, and/or other segmented anatomic structures in the 3D model, and apply any of the selection parameters described above to select a subset of the lymph nodes for biopsy. The selection parameters can be determined by the system (e.g., encoded in the system software) or can be manually set by the operator (e.g., the operator can choose which selection parameters should be applied). Once the system has selected the lymph node sites, the selection can be output to the operator for approval, rejection, or modification. Optionally, the operator can provide user input indicating which lymph node sites should be biopsied (e.g., via a graphical user interface). For example, the operator can manually select certain anatomic zones or regions, and the system can subsequently identify and select lymph node sites within those regions. The operator can also manually select specific lymph node sites to be biopsied.

At step 240, a sequence for biopsying the selected lymph node sites is determined. The sequence can indicate the order in which the selected lymph node sites should be biopsied during the procedure. In some embodiments, the sequence is configured to reduce the likelihood of cross-contamination between lymph node sites (e.g., transferring malignant cells to a non-cancerous lymph node). Accordingly, the sequence can include biopsying lymph node sites that are less likely to be positive for malignancy (e.g., sites that are located farther away and/or upstream from the target lesion) before lymph node sites that are more likely to be positive (e.g., sites that are located closer to and/or downstream from the target lesion). For example, the biopsy sequence can include sampling N3 nodes before N2 nodes, and N2 nodes before N1 nodes. As another example, the biopsy sequence can include sampling peripheral lymph node sites before central lymph node sites.

In some embodiments, the sequence is based, at least partly, on a trajectory for navigating the biopsy device to a target lesion. The trajectory can be a predetermined route that traverses anatomic passageways to reach the target lesion, and can be automatically, semi-automatically, or manually generated during preoperative planning for the biopsy procedure. In such embodiments, if the trajectory passes near one or more of the selected lymph node sites, biopsy samples can be collected from those sites in the order they are encountered (e.g., as the biopsy device moves towards the target lesion). Alternatively or in combination, the sequence can also be determined based on any of the following considerations: reducing backtracking, reducing total distance traversed by the biopsy device, reducing total time for the biopsy procedure, avoiding passageways that are inaccessible to the biopsy device or otherwise difficult to navigate, and/or avoiding having the biopsy device pass through areas that are close to vulnerable anatomic structures (e.g., major blood vessels, lung pleura, large bullae).

In some embodiments, step 240 also includes generating at least one proposed path for navigating a biopsy device within the anatomic region to reach each of the selected lymph node sites. The path can be configured to traverse the anatomic passageways between the selected lymph node sites so that the biopsy device reaches the sites in the correct sequence simply by following path. Optionally, the path can also include a route for navigating the biopsy device to the target lesion, as discussed above. The path can be generated in various ways, such as automatically, semi-automatically, or manually. For example, an operator can manually create some or all of the path by selecting passageways (e.g., airways) within the model via a suitable graphical user interface. Alternatively or in combination, some or all of the path can be generated automatically by the system. For instance, the system can use the model to identify and select passageways that are located close to the selected lymph node sites and are accessible to the biopsy device (e.g., have a sufficiently large diameter). In some embodiments, the system automatically generates a proposed path, and the operator can either approve the path or manually revise the path (e.g., by adding, deleting, or otherwise modifying portions of the path). Conversely, the operator can manually create a path, and the system can automatically revise the path or propose revisions for approval by the operator.

Optionally, the path can include an exit location near each selected lymph node site. The exit location can correspond to a point where the biopsy device exits the passageways to reach the lymph node site (e.g., by puncturing through the lumen of the passageway at the exit location). For example, the exit location can be a point in the passageway that is closest to the site. The path can further include a path segment connecting the exit location to the lymph node site (referred to herein as an "exit segment"). The length of the exit segment can be configured to be less than or equal to the maximum insertion depth of the biopsy device. For example, some biopsy needles may not be able to perform a biopsy of a target that is more than 3 cm from the exit location.

In some embodiments, the path is configured to avoid one or more vulnerable anatomic structures, such as vessels, lung pleura, large bullae, etc. For example, puncturing the lung pleura during the biopsy procedure could cause pneumothorax and/or other conditions that are dangerous to the patient. Accordingly, the path, exit locations, and/or exit segments can be constrained to avoid vulnerable anatomic structures. This can be accomplished, for example, by defining one or more hazard fences surrounding the vulnerable anatomic structures that are used to denote locations that the path cannot contact and/or overlap. The hazard fences can be created automatically, semi-automatically, or manually by the operator. Additional techniques for creating paths within an anatomic region are described in further detail in U.S. Patent Application Publication No. 2020/0030044 (filed Apr. 18, 2018) (disclosing a graphical user interface for planning a procedure), which is incorporated by reference herein in its entirety.

The output of the method 200 (e.g., the 3D model, selected lymph node sites, biopsy sequence, and/or path) can be saved (e.g., as one or more digital files) as part of a plan for the biopsy procedure. In embodiments where the plan is created on a preoperative planning workstation, the plan can be transferred to a medical instrument system that will be used to perform the biopsy procedure. Subsequently, during the biopsy procedure, the 3D model, selected lymph node sites, and/or biopsy sequence can be displayed to the operator (e.g., via a graphical user interface) to provide visual guidance and instructions for navigating to the selected biopsy sites, at described in greater detail below.

Although the steps of the method 200 are discussed and illustrated in a particular order, a person of ordinary skill in the relevant art will recognize that the method 200 can be altered and still remain within these and other embodiments of the present technology. In other embodiments, for example, the method 200 can be performed in a different order, e.g., any of the steps of the method 200 can be performed before, during, and/or after any of the other steps of the method 200. Additionally, one or more steps of the method 200 illustrated in FIG. 2 can be omitted (e.g., steps 220 or 240). Optionally, one or more steps of the method 200 can be repeated. For example, step 240 can be performed multiple times to generate multiple different sequences and/or paths for navigating the biopsy device to the selected lymph node sites. The operator can then select the sequence and/or path to be used, e.g., during the preoperative planning phase or during the actual biopsy procedure.

Figure 4:
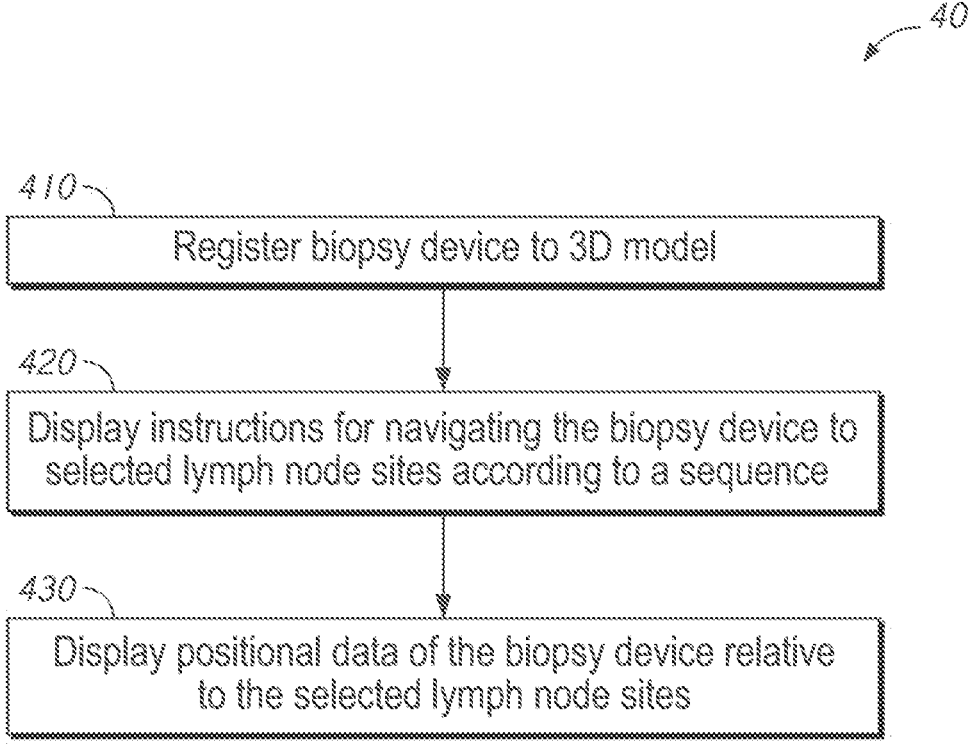
FIG. 4 is a flow diagram illustrating a method for performing a biopsy procedure in accordance with various embodiments of the present technology.

FIG. 4 is a flow diagram illustrating a method 400 for performing a biopsy procedure in accordance with various embodiments of the present technology. In some embodiments, the biopsy procedure is an image-guided procedure that uses an anatomic model to assist an operator in navigating a biopsy device to one or more target locations within the patient (e.g., to the locations of one or more lymph node sites). In some embodiments, the method 400 is performed after a preoperative plan for the biopsy procedure has been generated. For example, the method 400 can be performed after some or all of the steps of the method 200 of FIG. 2.

The method 400 is illustrated as a set of steps or processes 410-430. The method 400 can be performed by a suitable computing system or device (e.g., a medical instrument system, etc.). For example, all or a subset of the steps of the method 400 can be implemented by a control system of a medical instrument system or device, including various components or devices of a robotic or teleoperated system as described further below. The computing system for implementing the method 400 can include one or more processors operably coupled to a memory storing instructions that, when executed, cause the computing system to perform operations in accordance with the steps 410-430.

The method 400 begins at step 410 with registering a biopsy device to a 3D model of the patient's anatomy. Registration of the biopsy device to the 3D model can allow the position of the biopsy device within the patient to be tracked and mapped to a corresponding position within the model, thus providing visual guidance for navigating the biopsy device within the anatomy. Registration can be performed using survey data (e.g., positional and/or shape data) generated by one or more sensors in the biopsy device as the biopsy device is driven within different passageways in the anatomy. The survey data can be rotated, translated, or otherwise manipulated by rigid and/or non-rigid transformations to align them with the data points of the model. The registrations may be performed, for example, using a point-based iterative closest point (ICP) technique, as described in U.S. Provisional Pat. App. Nos. 62/205,440 and No. 62/205, 433, which are both incorporated by reference herein in their entireties. In other embodiments, however, the registration can be performed using other registration techniques.

At step 420, the system displays instructions for navigating the biopsy device to one or more lymph node sites. The lymph node sites can be selected during preoperative planning for the biopsy procedure, as previously described with respect to the method 200 of FIG. 2. During the biopsy procedure, the system can output a graphical representation of the lymph node sites via a suitable graphical user interface. For example, the lymph node sites can be rendered as opaque objects within the 3D model, while other anatomic structures of the model (e.g., airways, vessels) may be rendered as transparent or semi-transparent objects so that the lymph node sites remain visible. As another example, the lymph node sites can be displayed as points or images on a 2D map of the anatomic region. Alternatively or in combination, the system can output textual, audio, or other instructions that direct the operator to navigate the biopsy device to the selected lymph node sites. For instance, the system can instruct the operator to biopsy lymph nodes within certain lymph node stations, biopsy lymph nodes located within particular anatomic zones or regions of the anatomy, and so on.

In some embodiments, step 420 also includes displaying instructions for biopsying the selected lymph node sites according to a specified sequence. The sequence can be determined during preoperative planning for the biopsy procedure, as previously described with respect to the method 200 of FIG. 2. The sequence can be output to the operator in various ways, such as via the same graphical user interface used to display the lymph node sites. For example, the sequence can be graphically represented as a path that connects the selected lymph node sites in the desired order, as discussed above with respect to the method 200 of FIG. 2. The path can be overlaid onto the model and/or images of the actual patient anatomy to provide visual guidance as the operator navigate the biopsy device within the anatomic region. Alternatively or in combination, the system can output textual, audio, or other instructions that direct the operator to biopsy lymph node sites in a particular order and/or direct the operator to navigate the biopsy device along the path (e.g., in a particular direction and/or for a particular distance, with respect to particular anatomic landmarks, etc.).

At step 430, the method 400 displays positional data of the biopsy device relative to the selected lymph node sites. As discussed above, once the biopsy device has been registered to the anatomic model, the position of the biopsy device within the patient can be mapped to a corresponding position within the model. Accordingly, the position of the biopsy device relative to the lymph node sites can also be tracked and displayed. For example, the position of the biopsy device can be graphically represented as an object within the 3D anatomic model so the operator can visualize the location of the biopsy device relative to the lymph node sites and/or the planned path. The positional data can also be used to monitor the progress of the biopsy procedure, track which lymph node sites have or have not been biopsied, or otherwise provide instructions and/or feedback to assist the operator in performing the procedure. For example, the operator can be alerted if a lymph node site was missed, if a lymph node site was biopsied out of sequence, if the biopsy device is no longer on the correct path, etc.

Optionally, the method 400 can further include receiving feedback from the operator during the biopsy procedure. For example, the operator can provide input indicating that one or more selected lymph node sites could not be biopsied, that one or more additional lymph node sites were biopsied, that a portion of the planned path was inaccessible, that an alternative path was used, etc. The plan for the biopsy procedure can be adjusted based on the operator feedback. For example, the system can change the lymph node sites to be biopsied (e.g., add or remove lymph node sites), change the biopsy sequence, change the path to reach the lymph node sites, or any other suitable modification. In embodiments where the operator has immediate access to the biopsy results (e.g., via rapid onsite cytopathology evaluation (ROSE)), the biopsy plan can be updated based on whether a particular lymph node site was positive or negative for malignancy. For example, the system can omit lymph node sites that are downstream of a negative biopsy site. The instructions displayed to the operator can be updated to reflect any changes to the biopsy plan.

Although the steps of the method 400 are discussed and illustrated in a particular order, a person of ordinary skill in the relevant art will recognize that the method 400 can be altered and still remain within these and other embodiments of the present technology. In other embodiments, for example, the method 400 can be performed in a different order, e.g., any of the steps of the method 400 can be performed before, during, and/or after any of the other steps of the method 400. Additionally, one or more steps of the method 400 illustrated in FIG. 4 can be omitted. Optionally, one or more steps of the method 400 can be repeated.

Figure 5:
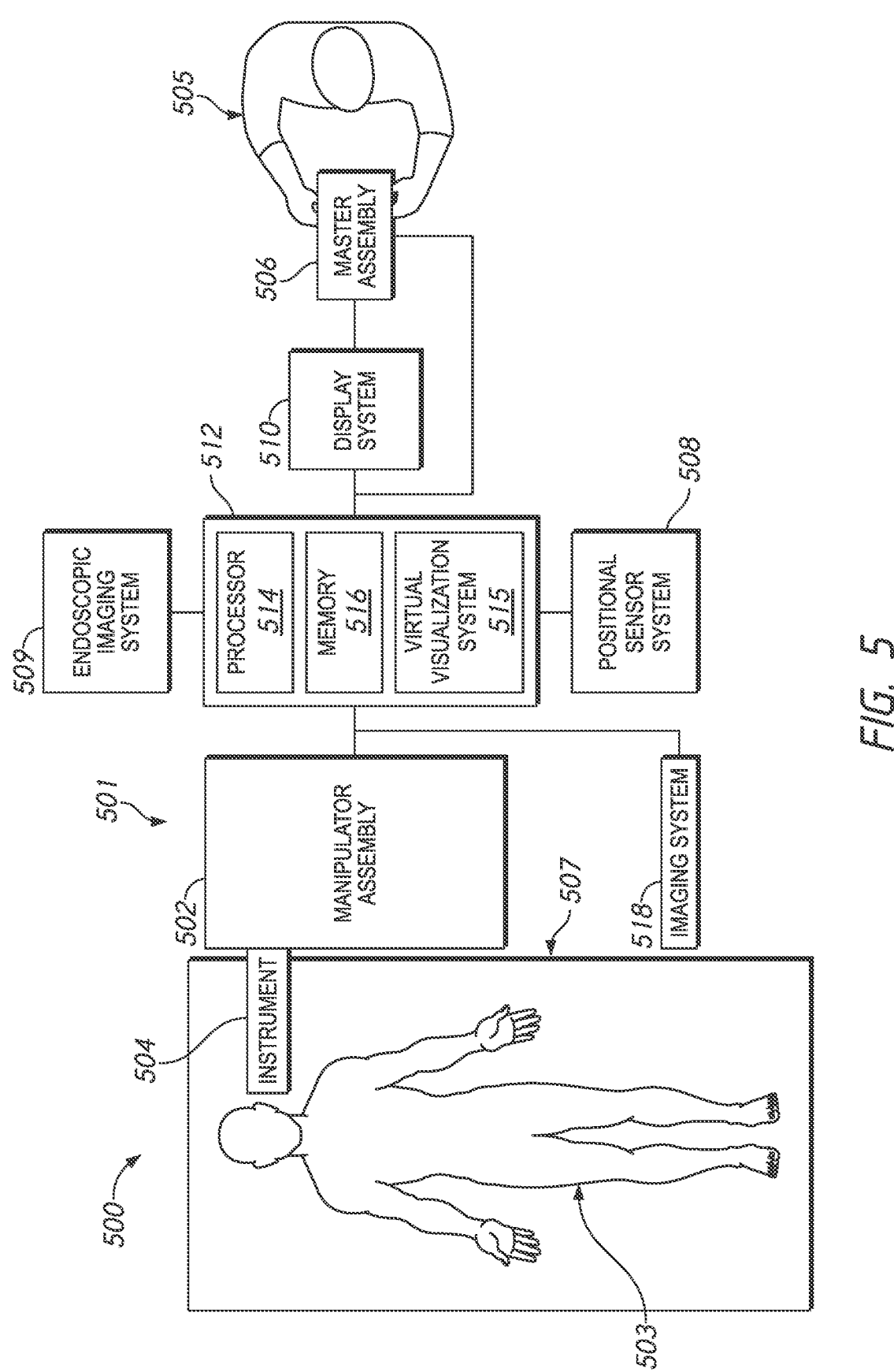
FIG. 5 is a schematic representation of a robotic or teleoperated medical system configured in accordance with various embodiments of the present technology.

B. Embodiments of Robotic or Teleoperated Medical Systems and Associated Devices, Systems, and Methods FIG. 5 is a schematic representation of a robotic or teleoperated medical system 500 ("medical system 500") configured in accordance with various embodiments of the present technology. The medical system 500 can be used with any of the procedures or methods described above with respect to FIGS. 1A-4. For example, the medical system 500 can be used to plan and/or perform a biopsy procedure on one or more lymph node sites, as previously discussed. As shown, the medical system 500 includes a manipulator assembly 502, a medical instrument system 504, a master assembly 506, and a control system 512. The manipulator assembly 502 supports the medical instrument system 504 and drives the medical instrument system 504 at the direction of the master assembly 506 and/or the control system 512 to perform various medical procedures on a patient 503 positioned on a table 507 in a surgical environment 501. In this regard, the master assembly 506 generally includes one or more control devices that can be operated by an operator 505 (e.g., a physician) to control the manipulator assembly 502. Additionally, or alternatively, the control system 512 includes a computer processor 514 and at least one memory 516 for effecting control between the medical instrument system 504, the master assembly 506, and/or other components of the medical system 500. The control system 512 can also include programmed instructions (e.g., a non-transitory computer-readable medium storing the instructions) to implement any one or more of the methods described herein, including instructions for providing information to a display system 510 and/or processing data for registration of the medical instrument system 504 with an anatomical model of the patient 503 (as described in greater detail below). The manipulator assembly 502 can be a teleoperated, a non-teleoperated, or a hybrid teleoperated and non-teleoperated assembly. Thus, all or a portion of the master assembly 506 and/or all or a portion of the control system 512 can be positioned inside or outside of the surgical environment 501.

To aid the operator 505 in controlling the manipulator assembly 502 and/or the medical instrument system 504 during an image-guided medical procedure, the medical system 500 may further include a positional sensor system 508, an endoscopic imaging system 509, an imaging system 518, and/or a virtual visualization system 515. In some embodiments, the positional sensor system 508 includes a location sensor system (e.g., an electromagnetic (EM) sensor system) and/or a shape sensor system for capturing positional sensor data (e.g., position, orientation, speed, velocity, pose, shape, etc.) of the medical instrument system 504. In these and other embodiments, the endoscopic imaging system 509 includes one or more image capture devices (not shown) that record endoscopic image data that includes concurrent or real-time images (e.g., video, still images, etc.) of patient anatomy. Images captured by the endoscopic imaging system 509 may be, for example, 2D or 3D images of patient anatomy captured by an image capture device positioned within the patient 503, and are referred to hereinafter as "real navigational images."

In some embodiments, the medical instrument system 504 may include components of the positional sensor system 508 and/or components of the endoscopic imaging system 509. For example, components of the positional sensor system 508 and/or components of the endoscopic imaging system 509 can be integrally or removably coupled to the medical instrument system 504. Additionally, or alternatively, the endoscopic imaging system 509 can include a separate endoscope (not shown) attached to a separate manipulator assembly (not shown) that can be used in conjunction with the medical instrument system 504 to image patient anatomy. The positional sensor system 508 and/or the endoscopic imaging system 509 may be implemented as hardware, firmware, software, or a combination thereof that interact with or are otherwise executed by one or more computer processors, such as the computer processor(s) 514 of the control system 512.

The imaging system 518 of the medical system 500 may be arranged in the surgical environment 501 near the patient 503 to obtain real-time and/or near real-time images of the patient 503 before, during, and/or after a medical procedure. In some embodiments, the imaging system 518 includes a mobile C-arm cone-beam CT imaging system for generating 3D images. For example, the imaging system 518 can include a DynaCT imaging system from Siemens Corporation, or another suitable imaging system. In these and other embodiments, the imaging system 518 can include other imaging technologies, including MRI, fluoroscopy, thermography, ultrasound, OCT, thermal imaging, impedance imaging, laser imaging, nanotube X-ray imaging, and/or the like.

The virtual visualization system 515 of the control system 512 provides navigation and/or anatomy-interaction assistance to the operator 505 when controlling the medical instrument system 504 during an image-guided medical procedure. As described in greater detail below, virtual navigation using the virtual visualization system 515 can be based, at least in part, upon reference to an acquired preoperative or intra-operative dataset (e.g., based, at least in part, upon reference to data generated by the positional sensor system 508, the endoscopic imaging system 509, and/or the imaging system 518) of anatomic passageways of the patient 503. In some implementations, for example, the virtual visualization system 515 processes preoperative and/or intraoperative image data of an anatomic region of the patient 503 captured by the imaging system 518 to generate an anatomic model (not shown) of the anatomic region. The virtual visualization system 515 then registers the anatomic model to positional sensor data generated by the positional sensor system 508 and/or to endoscopic image data generated by the endoscopic imaging system 509 to (i) map the tracked position, orientation, pose, shape, and/or movement of the medical instrument system 504 within the anatomic region to a correct position within the anatomic model, and/or (ii) determine a virtual navigational image of virtual patient anatomy of the anatomic region from a viewpoint of the medical instrument system 504 at a location within the anatomic model corresponding to a location of the medical instrument system 504 within the patient 503.

The display system 510 can display various images or representations of patient anatomy and/or of the medical instrument system 504 that are generated by the positional sensor system 508, by the endoscopic imaging system 509, by the imaging system 518, and/or by the virtual visualization system 515. In some embodiments, the display system 510 and/or the master assembly 506 may be oriented so the operator 505 can control the manipulator assembly 502, the medical instrument system 504, the master assembly 506, and/or the control system 512 with the perception of telepresence.

As discussed above, the manipulator assembly 502 drives the medical instrument system 504 at the direction of the master assembly 506 and/or the control system 512. In this regard, the manipulator assembly 502 can include select degrees of freedom of motion that may be motorized and/or teleoperated and select degrees of freedom of motion that may be non-motorized and/or non-teleoperated. For example, the manipulator assembly 502 can include a plurality of actuators or motors (not shown) that drive inputs on the medical instrument system 504 in response to commands received from the control system 512. The actuators can include drive systems (not shown) that, when coupled to the medical instrument system 504, can advance the medical instrument system 504 into a naturally or surgically created anatomic orifice. Other drive systems may move a distal portion (not shown) of the medical instrument system 504 in multiple degrees of freedom, which may include three degrees of linear motion (e.g., linear motion along the X, Y, Z Cartesian axes) and three degrees of rotational motion (e.g., rotation about the X, Y, Z. Cartesian axes). Additionally, or alternatively, the actuators can be used to actuate an articulable end effector of the medical instrument system 504 (e.g., for grasping tissue in the jaws of a biopsy device and/or the like).

FIG. 6 is a schematic representation of the manipulator assembly 502, the medical instrument system 504, and the imaging system 518 of FIG. 5 within the surgical environment 501 and configured in accordance with various embodiments of the present technology. As shown in FIG. 6, the surgical environment 501 has a surgical frame of reference ($X_S$, $Y_S$, $Z_S$) in which the patient 503 is positioned on the table 507, and the medical instrument system 504 has a medical instrument frame of reference ($X_M$, $Y_M$, $Z_M$) within the surgical environment 501. During the medical procedure, the patient 503 may be stationary within the surgical environment 501 in the sense that gross patient movement can be limited by sedation, restraint, and/or other means. In these and other embodiments, cyclic anatomic motion of the patient 503, including respiration and cardiac motion, may continue unless the patient 503 is asked to hold his or her breath to temporarily suspend respiratory motion.

The manipulator assembly 502 includes an instrument carriage 626 mounted to an insertion stage 628. In the illustrated embodiment, the insertion stage 628 is linear, while in other embodiments, the insertion stage 628 is curved or has a combination of curved and linear sections. In some embodiments, the insertion stage 628 is fixed within the surgical environment 501. Alternatively, the insertion stage 628 can be movable within the surgical environment 501 but have a known location (e.g., via a tracking sensor (not shown) or other tracking device) within the surgical environment 501. In these alternatives, the medical instrument frame of reference ($X_M$, $Y_M$, $Z_M$) is fixed or otherwise known relative to the surgical frame of reference ($X_S$, $Y_S$, $Z_S$).

The medical instrument system 504 of FIG. 6 includes an elongate device 631, a medical instrument 632, an instrument body 635, at least a portion of the positional sensor system 508, and at least a portion of the endoscopic imaging system 509. In some embodiments, the elongate device 631 is a flexible catheter or other biomedical device that defines a channel or lumen 644. The channel 644 can be sized and shaped to receive the medical instrument 632 (e.g., via a proximal end 636 of the elongate device 631 and/or an instrument port (not shown)) and facilitate delivery of the medical instrument 632 to a distal portion 638 of the elongate device 631. The elongate device 631 is coupled to the instrument body 635, which in turn is coupled and fixed relative to the instrument carriage 626 of the manipulator assembly 502.

In operation, the manipulator assembly 502 can control insertion motion (e.g., proximal and/or distal motion along an axis A) of the elongate device 631 into the patient 503 via a natural or surgically created anatomic orifice of the patient 503 to facilitate navigation of the elongate device 631 through anatomic passageways of an anatomic region of the patient 503 and/or to facilitate delivery of a distal portion 638 of the elongate device 631 to or near a target location within the patient 503. For example, the instrument carriage 626 and/or the insertion stage 628 may include actuators (not shown), such as servomotors, that facilitate control over motion of the instrument carriage 626 along the insertion stage 628. Additionally, or alternatively, the manipulator assembly 502 in some embodiments can control motion of the distal portion 638 of the elongate device 631 in multiple directions, including yaw, pitch, and roll rotational directions (e.g., to navigate patient anatomy). To this end, the elongate device 631 may house or include cables, linkages, and/or other steering controls (not shown) that the manipulator assembly 502 can use to controllably bend the distal portion 638 of the elongate device 631. For example, the elongate device 631 can house at least four cables that can be used by the manipulator assembly 502 to provide (i) independent "up-down" steering to control a pitch of the distal portion 638 of the elongate device 631 and (ii) independent "left-right" steering of the elongate device 631 to control a yaw of the distal portion 638 of the elongate device 631.

The medical instrument 632 of the medical instrument system 504 can be used for medical procedures, such as for survey of anatomic passageways, surgery, biopsy, ablation, illumination, irrigation, and/or suction. Thus, the medical instrument 632 can include image capture probes, biopsy instruments or devices (e.g., biopsy needles, endobronchial ultrasound (EBUS) probes), laser ablation fibers, and/or other surgical, diagnostic, and/or therapeutic tools. For example, the medical instrument 632 can include an endoscope or other biomedical device having one or more image capture devices 647 positioned at a distal portion 637 of and/or at other locations along the medical instrument 632. In these embodiments, an image capture device 647 can capture one or more real navigational images or video (e.g., a sequence of one or more real navigational image frames) of anatomic passageways and/or other real patient anatomy while the medical instrument 632 is within an anatomic region of the patient 503.

As discussed above, the medical instrument 632 can be deployed into and/or be delivered to a target location within the patient 503 via the channel 644 defined by the elongate device 631. In embodiments in which the medical instrument 632 includes an endoscope or other biomedical device having an image capture device 647 at its distal portion 637, the image capture device 647 can be advanced to the distal portion 638 of the elongate device 631 before, during, and/or after the manipulator assembly 502 navigates the distal portion 638 of the elongate device 631 to a target location within the patient 503. In these embodiments, the medical instrument 632 can be used as a survey instrument to capture real navigational images of anatomic passageways and/or other real patient anatomy, and/or to aid an operator (not shown) to navigate the distal portion 638 of the elongate device 631 through anatomic passageways to the target location.

As another example, after the manipulator assembly 502 positions the distal portion 638 of the elongate device 631 proximate a target location within the patient 503, the medical instrument 632 can be advanced beyond the distal portion 638 of the elongate device 631 to perform a medical procedure at the target location. Continuing with this example, after all or a portion of the medical procedure at the target location is complete, the medical instrument 632 can be retracted back into the elongate device 631 and, additionally or alternatively, be removed from the proximal end 636 of the elongate device 631 or from another instrument port (not shown) along the elongate device 631.

As shown in FIG. 6, the positional sensor system 508 of the medical instrument system 504 includes a shape sensor 633 and a position measuring device 639. In these and other embodiments, the positional sensor system 508 can include other position sensors (e.g., accelerometers, rotary encoders, etc.) in addition to or in lieu of the shape sensor 633 and/or the position measuring device 639.

The shape sensor 633 of the positional sensor system 508 includes an optical fiber extending within and aligned with the elongate device 631. In one embodiment, the optical fiber of the shape sensor 633 has a diameter of approximately 200 µm. In other embodiments, the diameter of the optical fiber may be larger or smaller. The optical fiber of the shape sensor 633 forms a fiber optic bend sensor that is used to determine a shape, orientation, and/or pose of the elongate device 631. In some embodiments, optical fibers having Fiber Bragg Gratings (FBGs) can be used to provide strain measurements in structures in one or more dimensions. Various systems and methods for monitoring the shape and relative position of an optical fiber in three dimensions are described in further detail in U.S. Patent Application Publication No. 2006/0013523 (filed Jul. 13, 2005) (disclosing fiber optic position and shape sensing device and method relating thereto); U.S. Pat. No. 7,781,724 (filed on Sep. 26, 2006) (disclosing fiber-optic position and shape sensing device and method relating thereto); U.S. Pat. No. 7,772,541 (filed on Mar. 12, 2008) (disclosing fiber-optic position and/or shape sensing based on Rayleigh scatter); and U.S. Pat. No. 6,389,187 (filed on Jun. 17, 1998) (disclosing optical fiber bend sensors), which are all incorporated by reference herein in their entireties. In these and other embodiments, sensors of the present technology may employ other suitable strain sensing techniques, such as Rayleigh scattering, Raman scattering, Brillouin scattering, and Fluorescence scattering. In these and still other embodiments, the shape of the elongate device 631 may be determined using other techniques. For example, a history of the pose of the distal portion 638 of the elongate device 631 can be used to reconstruct the shape of elongate device 631 over an interval of time.

In some embodiments, the shape sensor 633 is fixed at a proximal point 634 on the instrument body 635 of the medical instrument system 504. In operation, for example, the shape sensor 633 measures a shape in the medical instrument reference frame $(X_M, Y_M, Z_M)$ from the proximal point 634 to another point along the optical fiber, such as the distal portion 638 of the elongate device 631. The proximal point 634 of the shape sensor 633 may be movable along with instrument body 635 but the location of proximal point 634 may be known (e.g., via a tracking sensor (not shown) or other tracking device).

The position measuring device 639 of the positional sensor system 508 provides information about the position of the instrument body 635 as it moves along the insertion axis A on the insertion stage 628 of the manipulator assembly 502. In some embodiments, the position measuring device 639 includes resolvers, encoders, potentiometers, and/or other sensors that determine the rotation and/or orientation of actuators (not shown) controlling the motion of the instrument carriage 626 of the manipulator assembly 502 and, consequently, the motion of the instrument body 635 of the medical instrument system 504.

FIG. 7 is a schematic representation of a portion of the medical instrument system 504 of FIG. 6 extended within an anatomic region 750 (e.g., human lungs) of the patient 503 in accordance with various embodiments of the present technology. In particular, FIG. 7 illustrates the elongate device 631 of the medical instrument system 504 extending within branched anatomic passageways 752 of the anatomic region 750. The anatomic passageways 752 include a trachea 754 and a plurality of bronchial tubes 756.

As shown in FIG. 7, the elongate device 631 has a position, orientation, pose, and shape within the anatomic region 750, all or a portion of which (in addition to or in lieu of movement, such as speed or velocity) can be captured as positional sensor data by the positional sensor system 508 of FIGS. 5 and 6 (e.g., by the shape sensor 633 and/or the position measuring device 639 (FIG. 6)) to survey the anatomic passageways 752 of the anatomic region 750. In particular, the positional sensor system 508 can survey the anatomic passageways 752 by gathering positional sensor data of the medical instrument system 504 within the anatomic region 750 in the medical instrument frame of reference ($X_M$, $Y_M$, $Z_M$). The positional sensor data may at least in part be recorded as a set of 2D or 3D coordinate points. In the example of the anatomic region 750 being human lungs, the coordinate points may represent the locations of the distal portion 638 of the elongate device 631 and/or of other portions of the elongate device 631 while the elongate device 631 is advanced through the trachea 754 and the bronchial tubes 756. In these and other embodiments, the collection of coordinate points may represent the shape(s) of the elongate device 631 while the elongate device 631 is advanced through the anatomic region 750. In these and still other embodiments, the coordinate points may represent positional data of other portions (e.g., the medical instrument 632 (FIG. 6)) of the medical instrument system 504.

The coordinate points may together form a point cloud. For example, FIG. 8 illustrates a plurality of coordinate points 862 forming a point cloud 860 representing a shape of the elongate device 631 of FIG. 7 while the elongate device 631 is within the anatomic region 750 (FIG. 7) in accordance with various embodiments of the present technology. In particular, the point cloud 860 of FIG. 8 is generated from the union of all or a subset of the coordinate points 862 recorded by the positional sensor system 508 (FIG. 6) while the elongate device 631 is in the stationary position illustrated in FIG. 7.

In some embodiments, a point cloud (e.g., the point cloud 860) can include the union of all or a subset of coordinate points recorded by the positional sensor system 508 during an image capture period that spans multiple shapes, positions, orientations, and/or poses of the elongate device 631 within the anatomic region 750. In these embodiments, the point cloud can include coordinate points captured by the positional sensor system 508 that represent multiple shapes of the elongate device 631 while the elongate device 631 is advanced or moved through patient anatomy during the image capture period. Additionally, or alternatively, because the configuration, including shape and location, of the elongate device 631 within the patient 503 may change during the image capture period due to anatomical motion, the point cloud in some embodiments can comprise a plurality of coordinate points 862 captured by the positional sensor system 508 that represent the shapes of the elongate device 631 as the elongate device 631 passively moves within the patient 503. As described in greater detail below, a point cloud of coordinate points captured by the positional sensor system 508 can be registered to different models or datasets of patient anatomy.

Referring again to FIG. 6, the endoscopic imaging system 509 of the medical instrument system 504 includes one or more image capture devices 647 configured to capture one or more real navigational images of real patient anatomy (e.g., the anatomic passageways 752 of FIG. 7) while the elongate device 631 and/or the medical instrument 632 is within an anatomic region (e.g., the anatomic region 750 of FIG. 7) of the patient 503. For example, the endoscopic imaging system 509 can include an image capture device 647 positioned at the distal portion 637 of the medical instrument 632. In these and other embodiments, the endoscopic imaging system 509 can include one or more image capture devices (not shown) positioned at other locations along the medical instrument 632 and/or along the elongate device 631 (e.g., at the distal portion 638 of the elongate device 631).

In the embodiment illustrated in FIG. 7, the image capture device 647 of the medical instrument 632 (FIG. 6) is advanced to and positioned at the distal portion 638 of the elongate device 631. In this embodiment, the image capture device 647 can survey the anatomic passageways 752 by capturing real navigational images of the anatomic passageways 752 while the elongate device 631 is navigated through the trachea 754 and the bronchial tubes 756 of the anatomic region 750.

FIG. 9 is an example of a real navigational image 970 (e.g., a still image, an image frame of a video, etc.) of patient anatomy of the anatomic region 750 of FIG. 7 (such as one of the anatomic passageways 752) captured via the image capture device 647 (FIG. 7). As shown, the real navigational image 970 shows a branching point or carina 971 of two anatomic passageways 752 within the anatomic region 750 from a viewpoint of the medical instrument 632 (FIG. 6). In this example, because the image capture device 647 is positioned at the distal portions 637 and 638 of the medical instrument 632 and the elongate device 631 (FIG. 7), respectively, the viewpoint of the real navigational image 970 is from the distal portion 637 of the medical instrument 632 such that the medical instrument 632 and the elongate device 631 are not visible within the real navigational image 970. In other embodiments, the image capture device 647 can be positioned at another location along the medical instrument 632 and/or along the elongate device 631 (FIGS. 6 and 7). In these embodiments, the endoscopic imaging system 99 (FIG. 6) can capture real navigational images from a corresponding viewpoint of the medical instrument 632 and/or of the elongate device 631. A portion of the medical instrument 632 and/or of the elongate device 631 may be visible within these real navigational images depending on the positions of the medical instrument 632 and the elongate device 631 relative to one another.

Referring again to FIG. 6, the real navigational images captured by the endoscopic imaging system 509 can facilitate navigation of the distal portion 638 of the elongate device 631 through patient anatomy (e.g., through the anatomic passageways 752 of FIG. 7) and/or delivery of the distal portion 638 of the elongate device 631 to a target location within the patient 503. In these and other embodiments, the real navigational images captured by the endoscopic imaging system 509 can facilitate (i) navigation of the distal portion 637 of the medical instrument 632 beyond the distal portion 638 of the elongate device 631, (ii) delivery of the distal portion 637 of the medical instrument

632 to a target location within the patient 503, and/or (iii) visualization of patient anatomy during a medical procedure. In some embodiments, each real navigational image captured by the endoscopic imaging system 509 can be associated with a time stamp and/or a position recorded in the medical instrument frame of reference ($X_M$, $Y_M$, $Z_M$). The real navigational images captured by the endoscopic imaging system 509 can optionally be used to improve a registration between a point cloud of coordinate points (e.g., the point cloud 860 of FIG. 8) generated by the positional sensor system 508 and image data captured by the imaging system 518.

As shown in FIG. 6, the imaging system 518 is arranged near the patient 503 to obtain 3D images of the patient 503 (e.g., of the anatomic region 750 of FIG. 7). In some embodiments, the imaging system 518 includes one or more imaging technologies, including CT, MRI, fluoroscopy, thermography, ultrasound, OCT, thermal imaging, impedance imaging, laser imaging, nanotube X-ray imaging, and/or the like. The imaging system 518 is configured to generate image data of patient anatomy before, during, and/or after the elongate device 631 is extended within the patient 503. Thus, the imaging system 518 can be configured to capture preoperative, intraoperative, and/or postoperative 3D images of patient anatomy. In these and other embodiments, the imaging system 518 may provide real-time or near real-time images of patient anatomy.

FIG. 10 illustrates an example of intraoperative image data 1080 of a portion 1055 of the anatomic region 750 of FIG. 7 captured during an image capture period by the imaging system 518 (FIG. 6) while the elongate device 631 of the medical instrument system 504 is extended within the anatomic region 750. As shown, the image data 1080 includes graphical elements 1081 representing the elongate device 631 and graphical elements 1082 representing the anatomic passageways 752 of the anatomic region 750.

All or a portion of the graphical elements 1081 and 1082 of the image data 1080 can be segmented and/or filtered to generate a virtual, 3D model of the anatomic passageways 752 within the portion 1055 of the anatomic region 750 (with or without the medical instrument system 504). In some embodiments, the graphical elements 1081 and 1082 can additionally or alternatively be segmented and/or filtered to generate an image point cloud (not shown) of the medical instrument system 504 based, at least in part, on images captured by the imaging system 108 (FIG. 6) while the medical instrument system 504 is within the anatomic region 750. During the segmentation process, pixels or voxels generated from the image data 1080 may be partitioned into segments or elements or be tagged to indicate that they share certain characteristics or computed properties such as color, density, intensity, and texture. The segments or elements may then be converted to an anatomic model and/or to an image point cloud of the medical instrument system 504. Additionally, or alternatively, the segments or elements can be used to locate (e.g., calculate) and/or define a center line or other points running along the anatomic passageways 752. The generated anatomic model and/or the image point cloud may be 2D or 3D and may be generated in an image reference frame ($X_I$, $Y_I$, $Z_I$).

As discussed above with respect to FIG. 5, the display system 510 (FIG. 5) of the medical system 500 (FIG. 5) can display various images or representations of patient anatomy and/or of the medical instrument system 504 based, at least in part, on data captured and/or generated by the positional sensor system 508, by the endoscopic imaging system 509, by the imaging system 518, and/or by the virtual visualization system 515. In various implementations, the images and/or representations can be utilized by the system to aid the operator 505 (FIG. 5) in conducting an image-guided medical procedure.

FIG. 11 is a schematic representation of an example display 1110 produced by the display system 510 (FIG. 5) in accordance with various embodiments of the present technology. As shown, the display 1110 includes a real navigational image 1170, a composite virtual navigational image 1191 (also referred to as a "composite virtual image 1191"), and a virtual navigational image 1192. The real navigational image 1170 can be substantially the same as the real navigational image 970 of FIG. 9. Thus, for example, the real navigational image 1170 can be captured by the endoscopic imaging system 509 (FIG. 6) and provided to the display system 510 (FIG. 5) to be presented on the display 1110 in real-time or near real-time. In the illustrated embodiment, the real navigational image 1170 illustrates real patient anatomy (e.g., a carina 1171 marking a branching point of two anatomic passageways 752) from a viewpoint oriented distally away from the distal portion 637 of the medical instrument 632 (FIG. 6).

The composite virtual image 1191 of FIG. 11 is displayed in the image reference frame ($X_I$, $Y_I$, $Z_I$) and includes an anatomic model 1150 generated from image data of the anatomic region 750 of FIG. 7 captured by the imaging system 518 (FIG. 6). The anatomic model 1150 is registered (i.e., dynamically referenced) with a point cloud of coordinate points (e.g., the point cloud 860 of FIG. 8) generated by the positional sensor system 508 (FIG. 6) to display a representation 1104 within the anatomic model 1150 of the tracked position, shape, pose, orientation, and/or movement of the medical instrument system 504 (e.g., of the elongate device 631 of FIG. 6) within the patient 503 (FIG. 6). In some embodiments, the composite virtual image 1191 is generated by the virtual visualization system 515 (FIG. 5) of the control system 512 (FIG. 5). Generating the composite virtual image 1191 involves registering the image reference frame ($X_I$, $Y_I$, $Z_I$) with the surgical reference frame ($X_S$, $Y_S$, $Z_S$) and/or to the medical instrument reference frame ($X_M$, $Y_M$, $Z_M$). This registration may rotate, translate, or otherwise manipulate by rigid and/or non-rigid transforms coordinate points of the point cloud (e.g., the coordinate points 862 of the point cloud 860 of FIG. 8) captured by the positional sensor system 508 to align the coordinate points with the anatomic model 1150. The registration between the image and surgical/instrument frames of reference may be achieved, for example, by using a point-based ICP technique, as described in U.S. Provisional Pat. App. Nos. 62/205,440 and No. 62/205,433, which are both incorporated by reference herein in their entireties. In other embodiments, the registration can be achieved using another point cloud registration technique.

Based, at least in part, on the registration, the virtual visualization system 515 can additionally or alternatively generate virtual navigational images (e.g., the virtual navigational image 1192 of FIG. 11) that include a virtual depiction of patient anatomy from a viewpoint of a virtual camera on the representation 1104 of the medical instrument system 504 (FIG. 7) within the anatomic model 1150. In the embodiment illustrated in FIG. 11, the virtual camera of the virtual navigational image 1192 is positioned at a distal portion 1137 of the representation 1104 such that (i) the virtual viewpoint of the virtual navigational image 1192 is directed distally away from the distal portion 1137 of the representation 1104 and (ii) the representation 1104 is not visible within the virtual navigational image 1192. In other embodiments, the virtual visualization system 515 can position the virtual camera (a) at another location along the representation 1104 and/or (b) in a different orientation such that the virtual navigational image 1192 has a corresponding virtual viewpoint. In some embodiments, depending on the position and orientation of the virtual camera and on the positions of the elongate device 631 and the medical instrument 632 relative to one another within the patient 503, the virtual visualization system 515 can render a virtual representation (not shown) of at least a portion of the elongate device 631 and/or of the medical instrument 632 into the virtual navigational image 1192.

In some embodiments, the virtual visualization system 515 can place the virtual camera within the anatomic model 1150 at a position and orientation corresponding to the position and orientation of the image capture device 647 within the patient 503 (FIG. 6). As further shown in FIG. 11, the virtual navigational image 1192 illustrates virtual patient anatomy, such as a carina 1101 marking a branching point of two anatomic passageways 1152 of the anatomic model 1150, from substantially the same location at which the real navigational image 1170 is captured by the image capture device 647 (FIG. 6). Thus, the virtual navigational image 1192 provides a rendered estimation of patient anatomy visible to the image capture device 647 at a given location within the anatomic region 750 of FIG. 7. Because the virtual navigational image 1192 is based, at least in part, on the registration of a point cloud generated by the positional sensor system 508 and image data captured by the imaging system 518, the correspondence between the virtual navigational image 1192 and the real navigational image 1170 provides insight regarding the accuracy of the registration and can be used to improve the registration. Furthermore, the real navigational images (e.g., the real navigational image 1170) captured by the endoscopic imaging system 509 (FIG. 6) can (a) provide information regarding the position and orientation of the medical instrument system 504 (FIG. 5) within the patient 503, (b) provide information regarding portions of an anatomic region actually visited by the medical instrument system, and/or (c) help identify patient anatomy (e.g., branching points of anatomic passageways) proximate the medical instrument system 504, any one or more of which can be used to improve the accuracy of the registration.

As further shown in FIG. 11, the virtual navigational image 1192 can optionally include a navigation path overlay 1199. In some embodiments, the navigation path overlay 1199 is used to aid an operator 505 (FIG. 5) to navigate the medical instrument system 504 (FIG. 5) through anatomic passageways of an anatomic region to a target location within a patient 503. For example, the navigation path overlay 1199 can illustrate a "best" path through an anatomic region for an operator 505 to follow to deliver the distal portions 637 and/or 638 of the medical instrument 632 and/or of the elongate device 631, respectively, to a target location within the patient 503. In some embodiments, the navigation path overlay 1199 can be aligned with a centerline of or another line along (e.g., the floor of) a corresponding anatomic passageway.

C. Examples

Several aspects of the present technology are set forth in the following examples. Although several aspects of the present technology are set forth in examples directed to systems, computer-readable mediums, and methods, any of these aspects of the present technology can similarly be set forth in examples directed to any of systems, computer-readable mediums, and methods in other embodiments.

1. A system for planning a medical procedure, the system comprising:
   a processor; and
   a memory operably coupled to the processor and storing instructions that, when executed by the processor, cause the system to perform operations comprising—
      receiving image data of an anatomic region of a patient, wherein the anatomic region includes a plurality of lymph nodes and a target lesion,
      generating a three-dimensional model of the anatomic region by segmenting the image data, wherein the three-dimensional model includes a plurality of segmented components corresponding to the plurality of lymph nodes and the target lesion,
      selecting a subset of the lymph nodes to be biopsied during the medical procedure based at least in part on a location of the target lesion in the three-dimensional model, and
      determining a sequence for navigating a biopsy device to locations of the subset of the lymph nodes during the medical procedure.

2. The system of claim 1 wherein the plurality of lymph nodes includes lymph nodes from a plurality of different lymph node stations.

3. The system of example 1 or example 2 wherein the segmenting of the image data is performed based at least partly on input from an operator.

4. The system of example 3 wherein the input from the operator includes a selection of one or more locations in the image data corresponding to one or more lymph nodes.

5. The system of example 3 wherein the input from the operator includes an acceptance or a rejection of one or more of the segmented components.

6. The system of example 1 or example 2 wherein the segmenting of the image data is performed at least partly using a machine learning algorithm.

7. The system of any one of examples 1-6 wherein the subset of the lymph nodes comprises one or more mediastinal lymph nodes.

8. The system of any one of examples 1-6 wherein the subset of the lymph nodes includes one or more lymph nodes located downstream along a lymphatic drainage pathway from the target lesion.

9. The system of any one of examples 1-6 wherein the subset of lymph nodes includes at least one lymph node located at a same side of the anatomic region as the target lesion and at least one lymph node located at an opposite side of the anatomic region as the target lesion.

10. The system of any one of examples 1-6 wherein the subset of the lymph nodes is selected based on one or more of the following: lymph node size, lymph node shape, lymph node location, location of the target lesion, physiology of the patient, a predicted risk score for metastasis, input from an operator, or clinical guidelines.

11. The system of any one of examples 1-10 wherein the determined sequence for navigating the biopsy device is configured to reduce cross-contamination between different lymph nodes.

12. The system of any one of examples 1-10 wherein the determined sequence for navigating the biopsy device comprises biopsying lymph nodes having a lower likelihood of malignancy before lymph nodes having a higher likelihood of malignancy.

13. The system of any one of examples 1-10 wherein the determined sequence for navigating the biopsy device comprises biopsying lymph nodes located away from the target lesion before lymph nodes located close to the target lesion.

14. The system of any one of examples 1-13 wherein the operations further comprise generating a path for navigating the biopsy device to the target lesion based at least in part on the three-dimensional model.

15. The system of any one of examples 1-14, further comprising a display configured to output a graphical representation of the three-dimensional model and the subset of the lymph nodes.

16. The system of example 15 wherein the operations further comprise outputting, via the display, instructions for navigating the biopsy device to the locations of the subset of the lymph nodes according to the sequence.

17. The system of examples 15 or 16, further comprising a sensor configured to generate positional data of the biopsy device, wherein the operations further comprise outputting, via the display, a graphical representation of the positional data together with the graphical representation of the subset of the lymph nodes.

18. A non-transitory, computer-readable medium storing instructions thereon that, when executed by one or more processors of a computing system, cause the computing system to perform operations comprising:

receiving image data of an anatomic region of a patient, wherein the anatomic region includes a plurality of lymph nodes and a target lesion;

generating a three-dimensional model of the anatomic region by segmenting the image data, wherein the three-dimensional model includes a plurality of segmented components corresponding to the plurality of lymph nodes and the target lesion;

selecting a subset of the lymph nodes to be biopsied during a medical procedure based at least in part on a location of the target lesion in the three-dimensional model; and determining a sequence for navigating a biopsy device to locations of the subset of the lymph nodes during the medical procedure.

19. The non-transitory, computer-readable medium of example 18 wherein the plurality of lymph nodes includes lymph nodes from a plurality of different lymph node stations.

20. The non-transitory, computer-readable medium of example 18 or example 19 wherein the operations further comprise receiving user input for performing the segmenting of the image data.

21. The non-transitory, computer-readable medium of example 20 wherein the user input includes a selection of one or more locations in the image data corresponding to one or more locations of the lymph nodes.

22. The non-transitory, computer-readable medium of example 20 wherein the input from the operator includes an acceptance or a rejection of one or more of the segmented components.

23. The non-transitory, computer-readable medium of example 18 or example 19 wherein the segmenting is performed at least partly using a machine learning algorithm.

24. The non-transitory, computer-readable medium of any one of examples 18-23 wherein the subset of the lymph nodes comprises one or more mediastinal lymph nodes.

25. The non-transitory, computer-readable medium of any one of examples 18-23 wherein the subset of the lymph nodes comprises one or more lymph nodes located downstream along a lymphatic drainage pathway from the target lesion.

26. The non-transitory, computer-readable medium of any one of examples 18-23 wherein the subset of lymph nodes includes at least one lymph node located at a same side of the anatomic region as the target lesion and at least one lymph node located at an opposite side of the anatomic region as the target lesion.

27. The non-transitory, computer-readable medium of any one of examples 18-23 wherein the subset of the lymph nodes is selected based on one or more of the following: lymph node size, lymph node shape, lymph node location, location of the target lesion, physiology of the patient, a predicted risk score for metastasis, input from an operator, or clinical guidelines.

28. The non-transitory, computer-readable medium of any one of examples 18-27 wherein the determined sequence for navigating the biopsy device is configured to reduce a likelihood of cross-contamination between lymph nodes.

29. The non-transitory, computer-readable medium of any one of examples 18-27 wherein the determined sequence for navigating the biopsy device comprises biopsying lymph nodes having a lower likelihood of malignancy before lymph nodes having a higher likelihood of malignancy.

30. The non-transitory, computer-readable medium of any one of examples 18-27 wherein the determined sequence for navigating the biopsy device comprises biopsying lymph nodes located away from the target lesion before lymph nodes located close to the target lesion.

31. The non-transitory, computer-readable medium of any one of examples 18-30 wherein the operations further comprise generating a path for navigating the biopsy device to the target lesion based at least in part on the three-dimensional model.

32. The non-transitory, computer-readable medium of any one of examples 18-31 wherein the operations further comprise outputting a graphical representation of the three-dimensional model and the subset of the lymph nodes.

33. The non-transitory, computer-readable medium of any one of examples 18-31 wherein the operations further comprise outputting instructions for navigating the biopsy device to the locations of the subset of the lymph nodes according to the sequence.

34. The non-transitory, computer-readable medium of any one of examples 18-31 wherein the operations further comprise:

receiving positional data of the biopsy device; and outputting a graphical representation of the positional data together with the graphical representation of the subset of the lymph nodes.

35. The non-transitory, computer-readable medium of any one of examples 18-34 wherein the three-dimensional model further includes additional segmented components corresponding to airways and lungs of the patient.

36. A method, comprising:

receiving image data of an anatomic region of a patient, wherein the anatomic region includes a plurality of lymph nodes and a target lesion;

generating a three-dimensional model of the anatomic region by segmenting the image data, wherein the three-dimensional model includes a plurality of segmented components corresponding to the plurality of lymph nodes and the target lesion;

selecting a subset of the lymph nodes to be biopsied during a medical procedure based at least in part on a location of the target lesion in the three-dimensional model; and determining a sequence for navigating a biopsy device to locations of the subset of the lymph nodes during the medical procedure.

D. Conclusion

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

Although many of the embodiments are described above in the context of navigating and performing medical procedures within lungs of a patient, other applications and other embodiments in addition to those described herein are within the scope of the present technology. For example, unless otherwise specified or made clear from context, the devices, systems, methods, and computer program products of the present technology can be used for various image-guided medical procedures, such as medical procedures performed on, in, or adjacent hollow patient anatomy, and, more specifically, in procedures for surveying, biopsying, ablating, or otherwise treating tissue within and/or proximal the hollow patient anatomy. Thus, for example, the systems, devices, methods, and computer program products of the present disclosure can be used in one or more medical procedures associated with other patient anatomy, such as the bladder, urinary tract, GI system, and/or heart of a patient.

As used herein, the term "operator" shall be understood to include any type of personnel who may be performing or assisting a medical procedure and, thus, is inclusive of a physician, a surgeon, a doctor, a nurse, a medical technician, other personnel or user of the technology disclosed herein, and any combination thereof. Additionally, or alternatively, the term "patient" should be considered to include human and/or non-human (e.g., animal) patients upon which a medical procedure is being performed.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. As another example, various components of the technology can be further divided into subcomponents, and/or various components and/or functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

What is claimed is:

1. A system for planning a medical procedure, the system comprising:

a processor; and a memory operably coupled to the processor and storing instructions that, when executed by the processor, cause the system to perform operations comprising:

receiving image data of an anatomic region of a patient, wherein the anatomic region includes a plurality of lymph nodes and a target lesion, generating a three-dimensional model of the anatomic region by segmenting the image data, wherein the three-dimensional model includes a plurality of segmented components corresponding to the plurality of lymph nodes and the target lesion, selecting a subset of the lymph nodes to be biopsied during the medical procedure based at least in part on a location of the target lesion in the three-dimensional model, and determining a sequence for navigating a biopsy device to locations of the subset of the lymph nodes during the medical procedure, wherein each lymph node of the subset of the lymph nodes to be biopsied is positioned along a navigation path to be traversed by the biopsy device.

2. The system of claim 1 wherein the plurality of lymph nodes includes lymph nodes from a plurality of different lymph node stations.

3. The system of claim 1 wherein the segmenting of the image data is performed based at least partly on input from an operator.

4. The system of claim 3 wherein the input from the operator includes a selection of one or more locations in the image data corresponding to one or more lymph nodes.

5. The system of claim 3 wherein the input from the operator includes an acceptance or a rejection of one or more of the segmented components.

6. The system of claim 1 wherein the segmenting of the image data is performed at least partly using a machine learning algorithm.

7. The system of claim 1 wherein the subset of the lymph nodes comprises one or more mediastinal lymph nodes.

8. The system of claim 1 wherein the subset of the lymph nodes includes one or more lymph nodes located downstream along a lymphatic drainage pathway from the target lesion.

9. The system of claim 1 wherein the subset of lymph nodes includes at least one lymph node located at a same side of the anatomic region as the target lesion and at least one lymph node located at an opposite side of the anatomic region as the target lesion.

10. The system of claim 1 wherein the subset of the lymph nodes is selected based on one or more of the following:

lymph node size, lymph node shape, lymph node location, location of the target lesion, physiology of the patient, a predicted risk score for metastasis, input from an operator, or clinical guidelines.

11. The system of claim 1 wherein the determined sequence for navigating the biopsy device is configured to reduce cross-contamination between different lymph nodes.

12. The system of claim 1 wherein the determined sequence for navigating the biopsy device comprises biopsying lymph nodes having a lower likelihood of malignancy before lymph nodes having a higher likelihood of malignancy.

13. The system of claim 1 wherein the operations further comprise generating the navigation path based at least in part on the three-dimensional model.

14. The system of claim 1, further comprising a display configured to output a graphical representation of the three-dimensional model and the subset of the lymph nodes.

15. The system of claim 14, further comprising a sensor configured to generate positional data of the biopsy device, wherein the operations further comprise outputting, via the display, a graphical representation of the positional data together with the graphical representation of the subset of the lymph nodes.

16. The system of claim 1 wherein a location of a first lymph node of the subset of lymph nodes in the sequence for navigating the biopsy device is further from the target lesion than a location of a second lymph node of the subset of lymph nodes.

17. A non-transitory, computer-readable medium storing instructions thereon that, when executed by one or more processors of a computing system, cause the computing system to perform operations comprising:

receiving image data of an anatomic region of a patient, wherein the anatomic region includes a plurality of lymph nodes and a target lesion;

generating a three-dimensional model of the anatomic region by segmenting the image data, wherein the three-dimensional model includes a plurality of segmented components corresponding to the plurality of lymph nodes and the target lesion;

selecting a subset of the lymph nodes to be biopsied during a medical procedure based at least in part on a location of the target lesion in the three-dimensional model; and determining a sequence for navigating a biopsy device to locations of the subset of the lymph nodes during the medical procedure, wherein each lymph node of the subset of the lymph nodes to be biopsied is positioned along a navigation path to be traversed by the biopsy device.

18. The non-transitory, computer-readable medium of claim 17 wherein the plurality of lymph nodes includes lymph nodes from a plurality of different lymph node stations.

19. The non-transitory, computer-readable medium of claim 17 wherein the operations further comprise receiving user input for performing the segmenting of the image data.

20. The non-transitory, computer-readable medium of claim 17 wherein the subset of the lymph nodes includes one or more lymph nodes located downstream along a lymphatic drainage pathway from the target lesion.

* * * * *